US008846020B2

(12) United States Patent
Seliktar et al.

(10) Patent No.: US 8,846,020 B2
(45) Date of Patent: Sep. 30, 2014

(54) SCAFFOLDS FORMED FROM POLYMER-PROTEIN CONJUGATES, METHODS OF GENERATING SAME AND USES THEREOF

(75) Inventors: Dror Seliktar, Haifa (IL); Yonatan Shachaf, Haifa (IL)

(73) Assignee: Regentis Biomaterials Ltd., Or-Akiva (IL)

( * ) Notice: Subject to any disclaimer, the term of this patent is extended or adjusted under 35 U.S.C. 154(b) by 0 days.

(21) Appl. No.: 13/515,298

(22) PCT Filed: Dec. 16, 2010

(86) PCT No.: PCT/IL2010/001072
§ 371 (c)(1),
(2), (4) Date: Jun. 12, 2012

(87) PCT Pub. No.: WO2011/073991
PCT Pub. Date: Jun. 23, 2011

(65) Prior Publication Data
US 2012/0258068 A1    Oct. 11, 2012

Related U.S. Application Data

(60) Provisional application No. 61/282,104, filed on Dec. 16, 2009.

(51) Int. Cl.
*A61K 47/48*    (2006.01)
*C08G 65/333*    (2006.01)
*C08L 89/00*    (2006.01)
*C12N 5/071*    (2010.01)

(52) U.S. Cl.
CPC ..................................... *A61K 47/48* (2013.01)
USPC ....... 424/78.17; 435/395; 435/375; 525/54.1; 524/612

(58) Field of Classification Search
None
See application file for complete search history.

(56) References Cited

U.S. PATENT DOCUMENTS

2006/0034889 A1    2/2006 Jo et al.

FOREIGN PATENT DOCUMENTS

| WO | WO 2005/061018 | | 7/2005 | | |
|---|---|---|---|---|---|
| WO | WO 2007/083875 | | 7/2007 | | |
| WO | WO 2007/107012 | | 9/2007 | | |
| WO | WO 2008/126092 | | 10/2008 | | |
| WO | WO 2009/142770 A2 | * | 11/2009 | ............... | C12N 5/08 |
| WO | WO 2009/1422770 | * | 11/2009 | ............. | A61K 47/48 |

OTHER PUBLICATIONS

Cohn et al. "Improved reverse thermo-responsive polymeric systems" (Aug. 2003) Biomaterials 24:3707-3714.*
Almany et al. "Biosynthetic hydrogel scaffolds made from fibrinogen and polyethylene glycol for 3D cell cultures" (Aug. 20, 2004) Biomaterials 26: 2467-2477.*
Chun et al. "The use of injectable, thermosensitive poly(organophosphazene)-RGD conjugates for the enhancement of mesenchymal stem cell osteogenic differentiation" (Aug. 27, 2009) Biomaterials 30(31): 6295-6308.*
Chan et al. "Scaffolding in tissue engineering: general approaches and tissue-specific considerations" (2008) Eur Spine J 17(Suppl 4):S467-S479.*
Almany (Biomaterials 2004; 26:2467-2477).*
Chan (Eur Spine J 17 2008; (Suppl 4): S 457-479).*
Cohn (Biomaterials 2003; 24:3707-3714).*
Chun (Biomaterials 2009; 30(31): 6295-6308).*
International Preliminary Report on Patentability Dated Jun. 28, 2012 From the International Bureau of WIPO Re. Application No. PCT/IL2010/001072.
International Search Report and the Written Opinion Dated Apr. 11, 2011 From the International Searching Authority Re. Application No. PCT/IL2010/001072.
Shachaf et al. "The Biocompatibility of Pluronic® F127 Fibrinogen-Based Hydrogels", Biomaterials, XO026882491, 31(10): 2836-2847, Apr. 1, 2010.
Stile et al. "Thermo-Responsive Peptide-Modified Hydrogels for Tissue Regeneration", Biomacromolecules, XP009140533, 2(1): 185-194, Feb. 8, 2001.
Yasuda et al. "In Vitro Culture of Chondrocytes in a Novel Thermoreversible Gelation Polymer Scaffold Containing Growth Factors", Tissue Engineering, XP002627187, 12(5): 1237-1245, May 2006. Abstract.
Yi et al. "Protein Conjugation With Amphiphilic Block Copolymers for Enhanced Cellular Delivery", Bioconjugate Chemistry, XP002627186, 19(5): 1071-1077, May 2008. Abstract.
Yoon et al. "Photo-Crosslinkable and Biodegradable Pluronic/Heparin Hydrogels for Local and Sustained Delivery of Angiogenic Growth Factor", Journal of Biomedical Materials Research, XP009145695, 83A(3): 597-605, Dec. 2007. Fig. 1.
Translation of Notification of Office Action Dated Apr. 2, 2013 From the State Intellectual Property Office of the People's Republic of China Re. Application No. 201080057801.1.
Translation of Search Report Dated Apr. 2, 2013 From the State Intellectual Property Office of the People's Republic of China Re. Application No. 201080057801.1.
Notification of Office Action Dated Dec. 5, 2013 From the State Intellectual Property Office of the People's Republic of China Re. Application No. 201080057801.1 and Its Translation Into English.
Search Report Dated Dec. 5, 2013 From the State Intellectual Property Office of the People's Republic of China Re. Application No. 201080057801.1 and Its Translation Into English.

* cited by examiner

*Primary Examiner* — Jean Witz
*Assistant Examiner* — Mindy Newman

(57) ABSTRACT

Conjugates are provided herein which comprise a protein attached to at least two polymeric moieties, at least one of which exhibits reverse thermal gelation. The conjugates are suitable for being cross-linked by non-covalent and/or covalent cross-linking. Compositions-of-matter comprising cross-linked conjugates are provided herein, as well as processes for producing same. Methods of controlling a physical property of compositions-of-matter are also provided herein. The conjugates and compositions-of-matter may be used for various applications, such as cell growth, tissue formation, and treatment of disorders characterized by tissue damage or loss, as described herein.

38 Claims, 22 Drawing Sheets
(19 of 22 Drawing Sheet(s) Filed in Color)

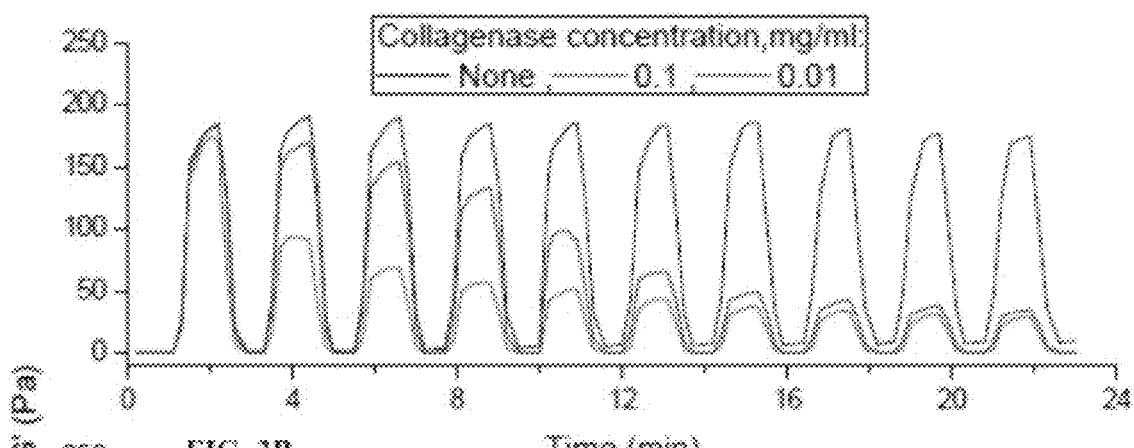
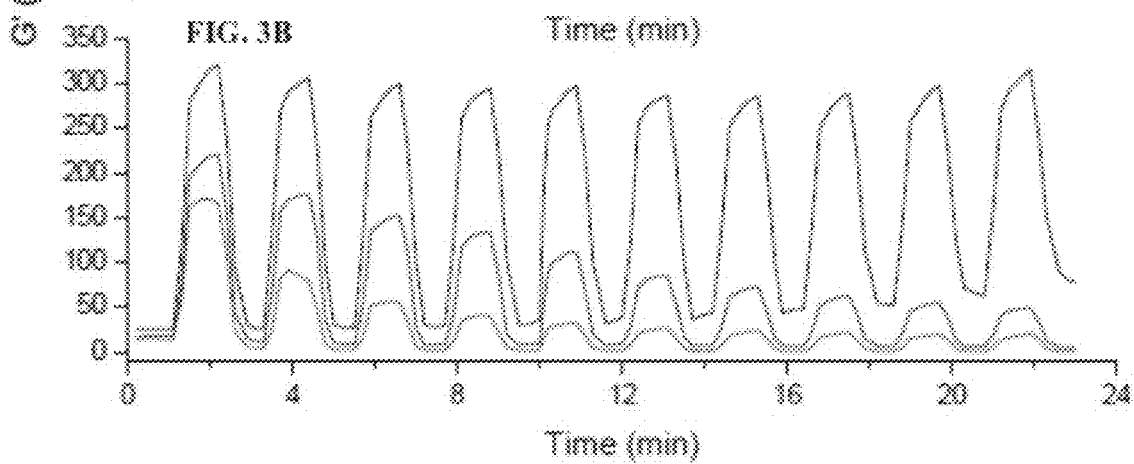
FIGs. 3A-B

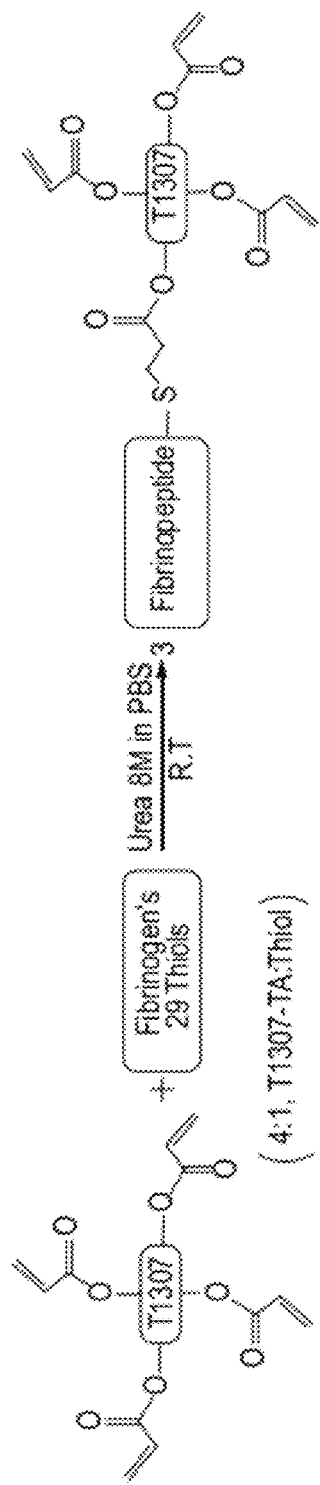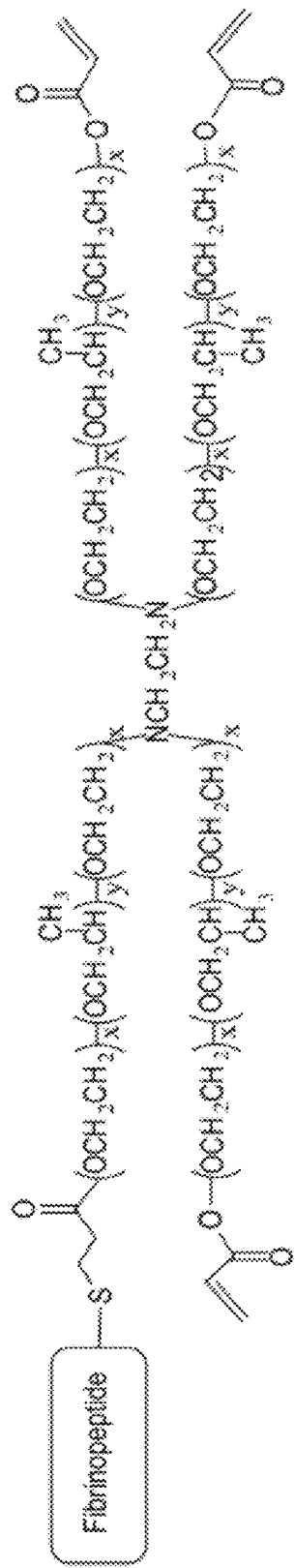
FIG. 13A
FIG. 13B

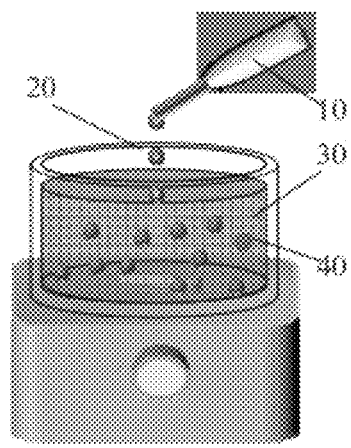
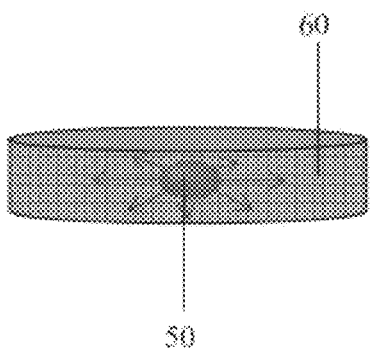
FIG. 23A
FIG. 23B
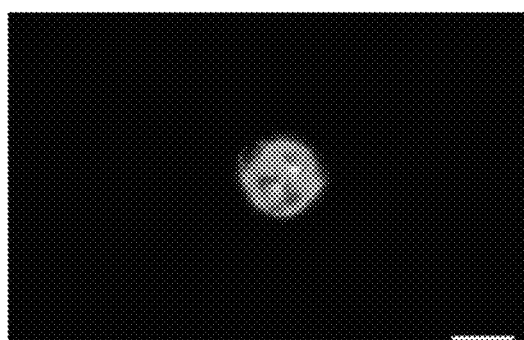
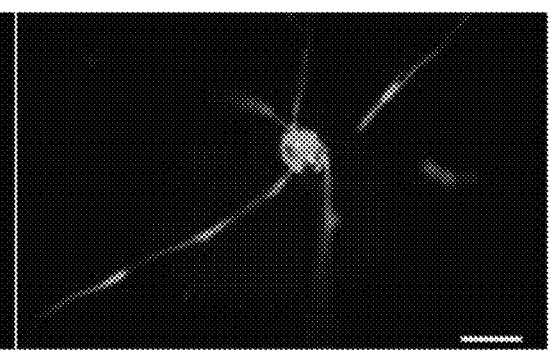
FIG. 24A
FIG. 24B
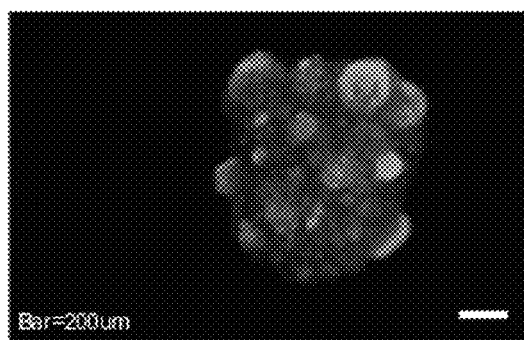
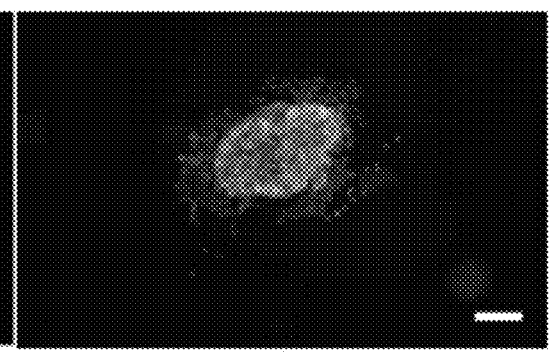
FIG. 25A
FIG. 25B

US 8,846,020 B2

SCAFFOLDS FORMED FROM POLYMER-PROTEIN CONJUGATES, METHODS OF GENERATING SAME AND USES THEREOF

RELATED APPLICATIONS

This application is a National Phase of PCT Patent Application No. PCT/IL2010/001072 having International filing date of Dec. 16, 2010, which claims the benefit of priority of U.S. Provisional Patent Application No. 61/282,104 filed on Dec. 16, 2009. The contents of the above applications are all incorporated herein by reference.

FIELD AND BACKGROUND OF THE INVENTION

The present invention, in some embodiments thereof, relates to polymer-protein conjugates and, more particularly, but not exclusively, to polymer-protein conjugates which form a scaffold, to processes of generating same and to uses thereof in, for example, tissue engineering.

As the field of tissue engineering evolves, there is a need for new biomaterial scaffolds that can provide more than just architectural and mechanical support. New "hybrid" materials are being developed as sophisticated scaffolds wherein biological polymers such as alginate, collagen or fibrinogen are combined with synthetic polymers to provide added versatility and bioactivity at the material/cell interface. From the perspective of cellular interactions, the biological domains of the hybrid material may actively participate in stimulating cells towards the formation of functional tissues. Bioactive signals are controlled via biological macromolecules such as protein segments [Cutler and Garcia, *Biomaterials* 2003, 24:1759-1770], growth factors [Seliktar et al., *J Biomed Mater Res A* 2004, 68:704-716; Zisch et al., *FASEB J* 2003; 17:2260-2262; DeLong et al., *Biomaterials* 2005, 26:3227-3234] or short bioactive peptides [Mann et al., *Biomaterials* 2001, 22:3045-3051; Lutolf et al., *Proc Natl Acad Sci USA* 2003, 100:5413-5418; Stile and Healy, *Biomacromolecules* 2001, 2:185494]. These elements are capable of influencing cell migration, proliferation, and guided differentiation [Dikovsky et al., *Biomaterials* 2006, 27:1496-1506]. From the perspective of biomaterial properties, "smart" polymers may also be used to provide better control over bulk features of the scaffold in response to changes in temperature, pH, or light [Furth et al., *Biomaterials* 2007, 28:5068-5073; Galaev and Mattiasson, *Trends Biotechnol* 1999, 17:335-340]. Hybrid materials made with smart polymers have additional degrees of freedom, including control over bulk density, degradability, porosity and compliance, all of which can be regulated by the synthetic polymer component [Peppas et al., *Annu Rev Biomed Eng* 2000, 2:9-29; Tsang and Bhatia, *Adv Drug Deliv Rev* 2004, 56:1635-1647; 3] Baier Leach et al., *Biotechnol Bioeng* 2003, 82:578-589].

Hybrid materials have been prepared based on conjugation of endogenous proteins with versatile synthetic polymers [Almany and Seliktar, *Biomaterials* 2005, 26:2467-2477; Gonen-Wadmany et al., *Biomaterials* 2007, 28:3876-3886; Peled et al., *Biomed Mater Res A* 2007, 80:874-884; Seliktar, *Ann NY Acad Sci* 2005, 1047:386-394]. The effect of alternating structural properties of hydrogels made from poly(ethylene glycol) (PEG) conjugated to fibrinogen on the morphology and remodeling of encapsulated smooth muscle cells has been investigated [Dikovsky et al., *Biomaterials* 2006, 27:1496-1506; Dikovsky et al., *Biophys J* 2008, 94:2914-2925]. These materials exhibited an ability to control cellular behavior by changing factors such as density, stiffness, and proteolytic degradability through the versatile synthetic component. The fibrinogen is a natural substrate for tissue remodeling which contains several cell signaling domains, including a protease degradation substrate and cell adhesion motifs [Herrick et al., *Int J Biochem Cell Biol* 1999, 31:741-746; Werb, *Cell* 1997, 91:439-442].

International Patent Application PCT/IL2004/001136 (published as WO2005/061018) and U.S. patent application Ser. No. 11/472,437 describe a biodegradable scaffold composed of a protein (e.g., fibrinogen) backbone cross-linked by a synthetic polymer such as poly(ethylene glycol), and methods of generating such scaffolds from polymer-protein conjugates.

International Patent Application PCT/IL2008/000521 (published as WO 2008/126092) describes scaffolds composed of albumin or thiolated collagen cross-linked by a synthetic polymer such as poly(ethylene glycol).

Reverse thermo-responsive polymers are capable of producing low viscosity aqueous solutions at ambient temperature, and forming a gel at a higher temperature. This property may be used to generate implants in situ [Cohn et al., *Biomacromolecules* 2005, 6:1168-1175].

Stile and Healy [*Biomacromolecules* 2001, 2:185-194] modified a smart polymer, N-isopropylacrylamide, with RGD (Arg-Gly-Asp) containing peptides to form a reversible thermo-sensitive hydrogel with bioactive segments for cell culture studies. They reported that the conjugation of RGD peptides to the thermo-responsive smart polymer does not compromise the temperature-induced sol-gel transition of the hydrogels. They further reported that the conjugated RGD peptide enhanced the biological interactions of the otherwise inert N-isopropylacrylamide polymer network.

Reverse thermo-responsive polymers having a poly(ethylene oxide) (PEO)-poly(propylene oxide) (PPO)-PEO triblock structure, referred to as "poloxamers", have also been reported. The endothermic sol-gel transition takes place due to an increase in entropy caused by release of water molecules bound to the PPO segments as temperature increases [Alexandridis, *Colloid Surface A* 1995, 96:1-46].

Pluronic® F127 poloxamer is a well known synthetic triblock copolymer ($PEO_{99}$-$PPO_{67}$-$PEO_{99}$) [Nagarajan and Ganesh, *J Colloid Interface Sci* 1996, 184:489-499; Sharma and Bhatia, *Int J Pharm* 2004, 278:361-377; Cohn et al., *Biomaterials* 2003, 24:3707-3714], that exhibits a reverse thermal gelation (RTG) property above a critical temperature in aqueous solutions. Cohn et al. [*Polym Adv Tech* 2007; 18:731-736] reported that polymerized F127 displays reverse thermal gelation at lower concentrations and with enhanced mechanical properties, as compared with F127.

Additional background art includes Halstenberg et al. [*Biomacromolecules* 2002, 3:710-723], Cohn et al. [*Polym Adv Tech* 2007; 18:731-736], and U.S. Pat. No. 7,842,667.

SUMMARY OF THE INVENTION

According to an aspect of some embodiments of the present invention there is provided a conjugate comprising a polypeptide having attached thereto at least two polymeric moieties, at least one of the polymeric moieties exhibiting a reverse thermal gelation.

According to an aspect of some embodiments of the present invention there is provided a composition-of-matter comprising a cross-linked form of a conjugate described herein, the cross-linked form comprising a plurality of molecules of the conjugate cross-linked to one another.

According to an aspect of some embodiments of the present invention there is provided a process of producing a composition-of-matter described herein, the process comprising heating a solution of a plurality of molecules of a conjugate described herein from a first temperature to a second temperature, the second temperature being such that a reverse thermal gelation of the conjugate in the solution is effected, thereby producing the composition-of-matter.

According to an aspect of some embodiments of the present invention there is provided a process of producing a composition-of-matter described herein, the process comprising subjecting a solution comprising a plurality of molecules of a conjugate described herein, the conjugate comprising at least one cross-linking moiety, to conditions that effect covalent cross-linking of the cross-linking moieties, thereby producing the composition-of-matter.

According to an aspect of some embodiments of the present invention there is provided a process of producing a composition-of-matter described herein in vivo, the process comprising:

(a) subjecting a solution comprising a plurality of molecules of a conjugate described herein, the conjugate comprising at least one cross-linking moiety, to conditions that effect covalent cross-linking ex vivo, to thereby produce a covalently cross-linked scaffold; and (b) subjecting the covalently cross-linked scaffold to a physiological temperature in vivo, such that a reverse thermal gelation of the scaffold is effected in vivo, thereby producing the composition-of-matter.

According to an aspect of some embodiments of the present invention there is provided a method of controlling a physical property of a composition-of-matter described herein, the method comprising controlling a parameter selected from the group consisting of a concentration of a conjugate described herein in solution, an ambient temperature, a presence or absence of an initiator, a dose of irradiation during covalent cross-linking, and a cross-linking temperature.

According to an aspect of some embodiments of the present invention there is provided a process of producing the conjugate described herein, the process comprising covalently attaching a polymer to a polypeptide, the polymer and the polypeptide being such that at least two polymer molecules covalently attach to a molecule of the polypeptide, wherein at least one of the two polymer molecules exhibits a reverse thermal gelation, thereby producing the conjugate.

According to an aspect of some embodiments of the present invention there is provided a use of a conjugate described herein or of a composition-of-matter described herein in the manufacture of a medicament for repairing tissue damage.

According to an aspect of some embodiments of the present invention there is provided a use of a conjugate described herein or of a composition-of-matter described herein in the manufacture of a medicament for treating a subject having a disorder characterized by tissue damage or loss.

According to an aspect of some embodiments of the present invention there is provided a method of inducing formation of a tissue in vivo, the method comprising implanting a composition-of-matter described herein in a subject, to thereby induce the formation of the tissue.

According to an aspect of some embodiments of the present invention there is provided a method of inducing formation of a tissue in vivo, the method comprising implanting a plurality of molecules of a conjugate described herein in a subject, to thereby induce the formation of the tissue.

According to an aspect of some embodiments of the present invention there is provided a method of inducing formation of a tissue ex vivo, the method comprising subjecting a composition-of-matter which comprises cells, as described herein, to conditions conductive to growth of the cells, to thereby induce tissue formation.

According to an aspect of some embodiments of the present invention there is provided a method of treating a subject having a disorder characterized by tissue damage or loss, the method comprising implanting a composition-of-matter described herein in a subject, to thereby induce formation of the tissue, thereby treating the disorder characterized by tissue damage or loss.

According to an aspect of some embodiments of the present invention there is provided a method of treating a subject having a disorder characterized by tissue damage or loss, the method comprising implanting a plurality of molecules of a conjugate described herein in a subject, to thereby induce formation of the tissue, thereby treating the disorder characterized by tissue damage or loss.

According to an aspect of some embodiments of the present invention there is provided a pharmaceutical, cosmetic or cosmeceutical composition comprising a plurality of molecules of a conjugate described herein, the composition being identified for use in inducing formation of a tissue upon being contacted with a tissue and further upon subjecting the composition to a physiological temperature.

According to an aspect of some embodiments of the present invention there is provided a kit for inducing formation of a tissue, the kit comprising:

(a) a conjugate described herein;
(b) an aqueous solvent; and
(c) instructions for cross-linking an aqueous solution the conjugate in order to form a scaffold for inducing formation of the tissue.

According to some embodiments of the invention, each of the polymeric moieties to exhibits a reverse thermal gelation.

According to some embodiments of the invention, at least one of the polymeric moieties further comprises at least one cross-linking moiety for covalently cross-linking a plurality of molecules of the conjugate to one another.

According to some embodiments of the invention, the conjugate is of the general formula:

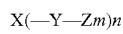

wherein:
X is a polypeptide described herein;
Y is a polymeric moiety described herein;
Z is a cross-linking moiety described herein;
n is an integer greater than 1; and
m is 0, 1 or an integer greater than 1.

According to some embodiments of the invention, the polypeptide comprises a protein or a fragment thereof.

According to some embodiments of the invention, the protein is selected from the group consisting of a cell signaling protein, an extracellular matrix protein, a cell adhesion protein, a growth factor, protein A, a protease, and a protease substrate.

According to some embodiments of the invention, the extracellular matrix protein is selected from the group consisting of fibrinogen, collagen, fibronectin, elastin, fibrillin, fibulin, vimentin, laminin and gelatin.

According to some embodiments of the invention, the polypeptide comprises a fibrinogen or a fragment thereof.

According to some embodiments of the invention, the protein is denatured.

According to some embodiments of the invention, the polypeptide is a denatured fibrinogen.

According to some embodiments of the invention, the polymeric moiety comprises a synthetic polymer.

According to some embodiments of the invention, at least one of the polymeric moieties comprises a poloxamer (poly(ethylene oxide-propylene oxide) copolymer).

According to some embodiments of the invention, each of the polymeric moieties comprises a poloxamer.

According to some embodiments of the invention, the poloxamer is F127 poloxamer.

According to some embodiments of the invention, at least one of the polymeric moieties comprises T1307 polymer.

According to some embodiments of the invention, the polymeric moieties are selected from the group consisting of a Pluronic® polymer and a Tetronic® polymer.

According to some embodiments of the invention, each of the polymeric moieties comprises from 1 to 10 of the cross linking moieties.

According to some embodiments of the invention, the cross-linking moiety comprises a polymerizable group.

According to some embodiments of the invention, the polymerizable group is polymerizable by free radical polymerization.

According to some embodiments of the invention, the polymerizable group is selected from the group consisting of an acrylate, a methacrylate, an acrylamide, a methacrylamide, and a vinyl sulfone.

According to some embodiments of the invention, the polypeptide is denaturated fibrinogen and the polymeric moieties comprise F127 poloxamer.

According to some embodiments of the invention, the conjugate comprises F127 poloxamer diacrylate moieties, wherein an acrylate group of each of the F127 poloxamer diacrylate moieties is attached to a cysteine residue of the fibrinogen.

According to some embodiments of the invention, the polypeptide is denaturated fibrinogen and the polymeric moieties comprise T1307 polymer.

According to some embodiments of the invention, the conjugate comprises T1307 tetraacrylate moieties, wherein an acrylate group of each of the T1307 tetraacrylate moieties is attached to a cysteine residue of the fibrinogen.

According to some embodiments of the invention, the conjugate is characterized by an ability to undergo reverse thermal gelation in an aqueous solution.

According to some embodiments of the invention, the reverse thermal gelation is effected at a concentration of less than 10 weight percents of the conjugate in the aqueous solution.

According to some embodiments of the invention, the reverse thermal gelation of the conjugate increases a shear storage modulus of the aqueous solution by at least ten-folds.

According to some embodiments of the invention, the reverse thermal gelation increases a shear storage modulus of the aqueous solution to at least 20 Pa.

According to some embodiments of the invention, the reverse thermal gelation increases a shear storage modulus of the aqueous solution from less than 2 Pa to at least 20 Pa.

According to some embodiments of the invention, the reverse thermal gelation occurs upon an increase of temperature from 10° C. to 55° C.

According to some embodiments of the invention, the reverse thermal gelation is reversible.

According to some embodiments of the invention, the reverse thermal gelation forms a biodegradable gel.

According to some embodiments of the invention, the conjugate is identified for use in generating a scaffold.

According to some embodiments of the invention, the conjugate is identified for use in reversibly generating a scaffold.

According to some embodiments of the invention, the scaffold is a hydrogel.

According to some embodiments of the invention, the hydrogel is characterized by a shear storage modulus of at least 15 Pa at a temperature of 37° C.

According to some embodiments of the invention, the hydrogel is capable of undergoing a reverse thermal gelation.

According to some embodiments of the invention, the composition-of-matter is a hydrogel.

According to some embodiments of the invention, the composition-of-matter is generated by a reverse thermal gelation of the plurality of molecules of the conjugate in an aqueous solution.

According to some embodiments of the invention, the plurality of molecules of the conjugate are non-covalently cross-linked to one another.

According to some embodiments of the invention, the cross-linked form of the conjugate is reversible.

According to some embodiments of the invention, at least one of the polymeric moieties comprises a cross-linking moiety, and the plurality of molecules of the conjugate are covalently cross-linked to one another.

According to some embodiments of the invention, the composition-of-matter is generated by subjecting a plurality of molecules of the conjugate to conditions for effecting cross-linking of the cross-linking moieties.

According to some embodiments of the invention, the composition-of-matter is characterized by a shear storage modulus of at least 20 Pa at a temperature of 37° C.

According to some embodiments of the invention, the composition-of-matter is capable of undergoing a reverse thermal gelation.

According to some embodiments of the invention, the reverse thermal gelation of the composition-of-matter increases a shear storage modulus of the composition-of-matter by at least 200%.

According to some embodiments of the invention, the reverse thermal gelation of the composition-of-matter increases a shear storage modulus of the composition-of-matter to at least 15 Pa.

According to some embodiments of the invention, the reverse thermal gelation of the composition-of-matter increases a shear storage modulus of the composition-of-matter from a first value in a range of from 0.5 Pa to 200 Pa to a second value which is at least 20% higher than the first value.

According to some embodiments of the invention, the reverse thermal gelation of the composition-of-matter increases a shear storage modulus of the composition-of-matter from a first value to a second value in a range of from 20 Pa to 5000 Pa, the second value being at least 20% higher than the first value.

According to some embodiments of the invention, the reverse thermal gelation of the composition-of-matter occurs upon an increase of temperature from 10° C. to 55° C.

According to some embodiments of the invention, the reverse thermal gelation of the composition-of-matter is reversible.

According to some embodiments of the invention, the composition-of-matter is to characterized by a shear storage modulus of one portion of the composition-of-matter that is different from a shear storage modulus of at least one other portion of the composition-of-matter.

According to some embodiments of the invention, the composition-of-matter is biodegradable.

According to some embodiments of the invention, the composition-of-matter further comprises cells therein.

According to some embodiments of the invention, the composition-of-matter is identified for use in inducing a formation of a tissue.

According to some embodiments of the invention, the composition-of-matter is identified for use in repairing tissue damage.

According to some embodiments of the invention, the composition-of-matter is produced in vivo.

According to some embodiments of the invention, the abovementioned second temperature is a physiological temperature.

According to some embodiments of the invention, the conjugate comprises at least one polymeric moiety that further comprises at least one cross-linking moiety, and the process further comprises subjecting the solution to conditions that effect cross-linking of the cross-linking moieties.

According to some embodiments of the invention, subjecting the solution to the conditions that effect cross-linking is effected prior to the heating.

According to some embodiments of the invention, subjecting the solution to the conditions that effect cross-linking is effected subsequent to the heating.

According to some embodiments of the invention, the covalent cross-linking is effected in vivo.

According to some embodiments of the invention, the covalent cross-linking is effected ex vivo, to thereby produce a covalently cross-linked scaffold, and the process further comprises subjecting the covalently cross-linked scaffold to a physiological temperature in vivo, such that a reverse thermal gelation of the scaffold is effected in vivo, thereby producing a composition-of-matter described herein.

According to some embodiments of the invention, the conditions comprise irradiation.

According to some embodiments of the invention, the conditions comprise a presence of a free radical initiator.

According to some embodiments of the invention, the solution further comprises cells, and the process is for producing a composition-of-matter comprising cells embedded therein.

According to some embodiments of the invention, the conjugate comprises at least one cross-linking moiety, and the method further comprises covalently cross-linking the plurality of molecules of the conjugate.

According to some embodiments of the invention, the cross-linking is effected by subjecting the plurality of molecules of the conjugate to conditions that effect covalent cross-linking of the cross-linking moiety.

According to some embodiments of the invention, the conjugate comprises at least one cross-linking moiety, and the composition described herein is identified for use in inducing formation of a tissue upon further subjecting the plurality of molecules of the conjugate to conditions that effect covalent cross-linking of the cross-linking moiety.

According to some embodiments of the invention, a pharmaceutical, cosmetic or cosmeceutical composition described herein further comprises an initiator for inducing covalent cross-linking of the cross-linking moiety.

According to some embodiments of the invention, a pharmaceutical, cosmetic or cosmeceutical composition described herein is packaged in a packaging material and identified in print, in or on the packaging material, for use in inducing formation of the tissue.

According to some embodiments of the invention, the conjugate comprises at least one cross-linking moiety, and the kit further comprises an initiator for inducing covalent cross-linking of the cross-linking moiety.

According to some embodiments of the invention, the kit further comprises cells for embedding in the scaffold described herein.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1A:
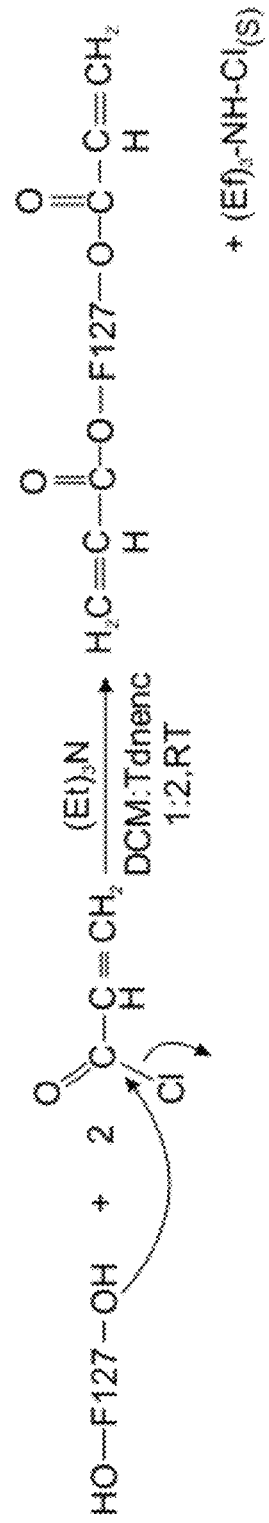
Figure 1B:
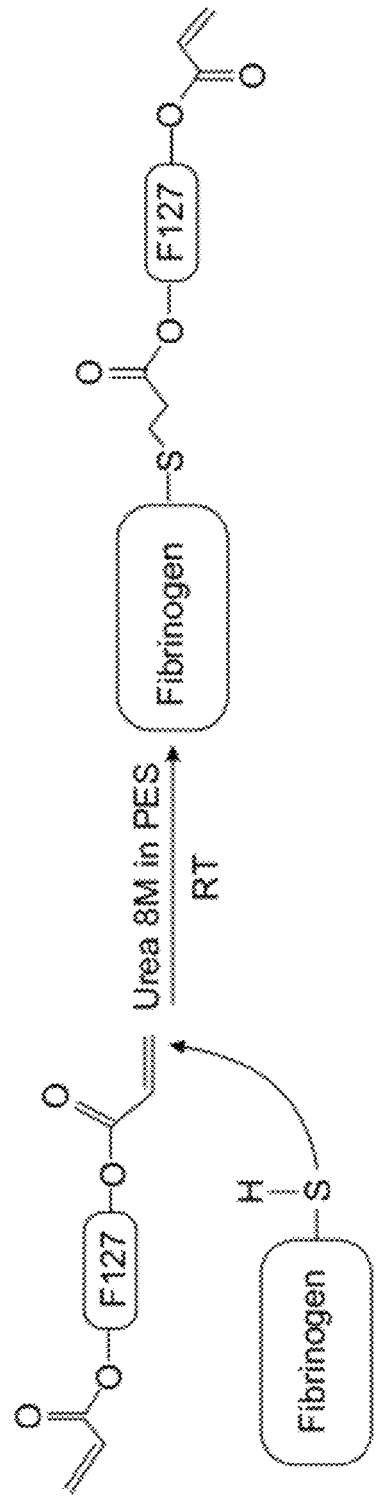
Figure 2:
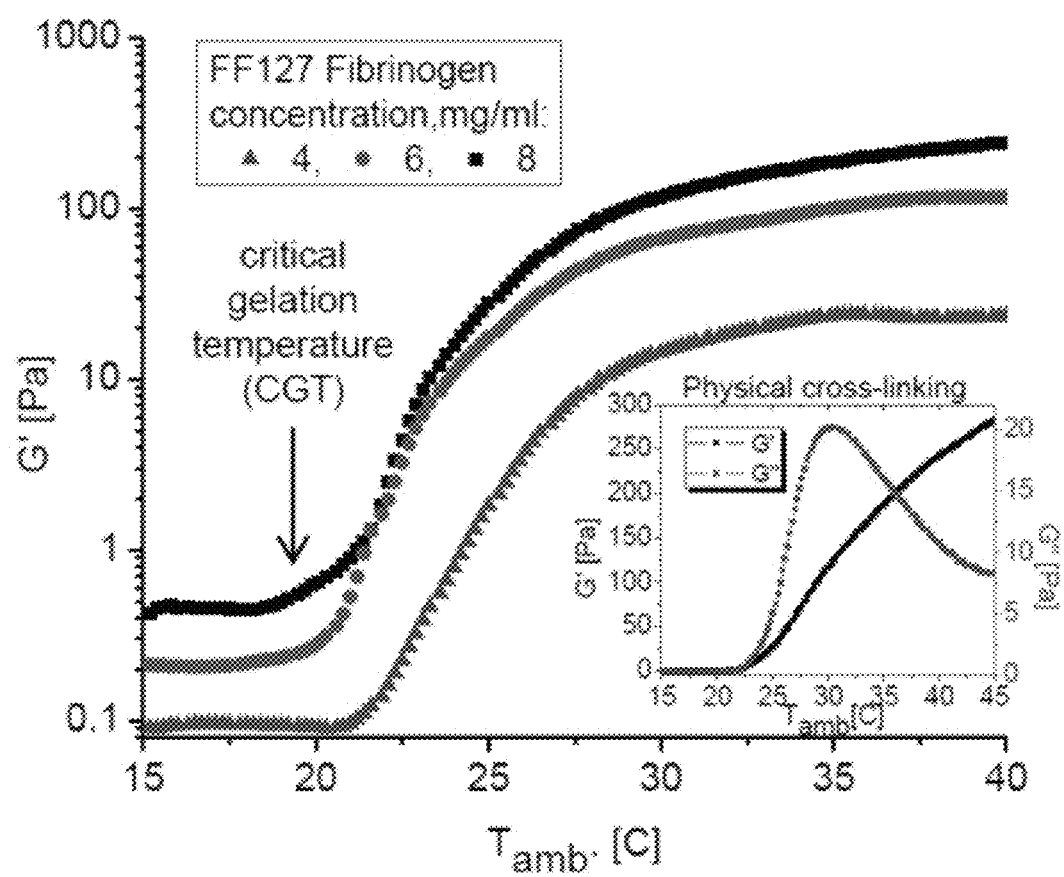
Figure 4:
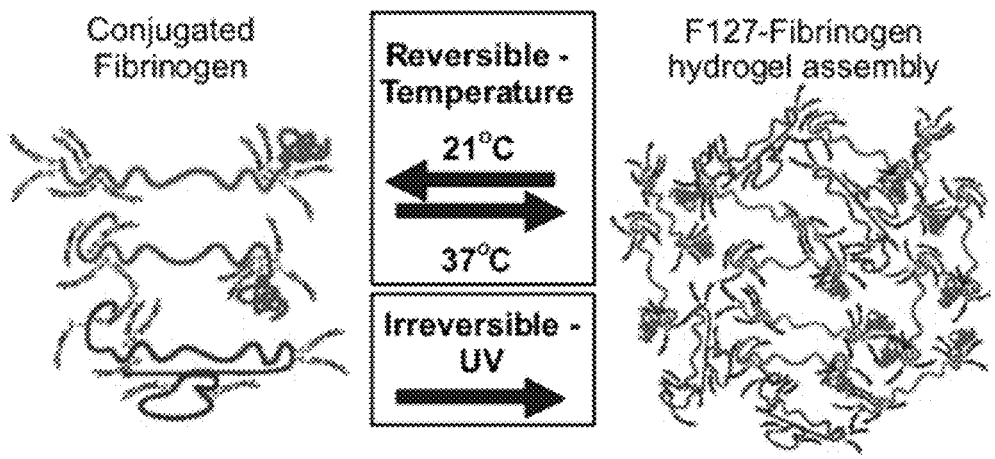
Figure 5:
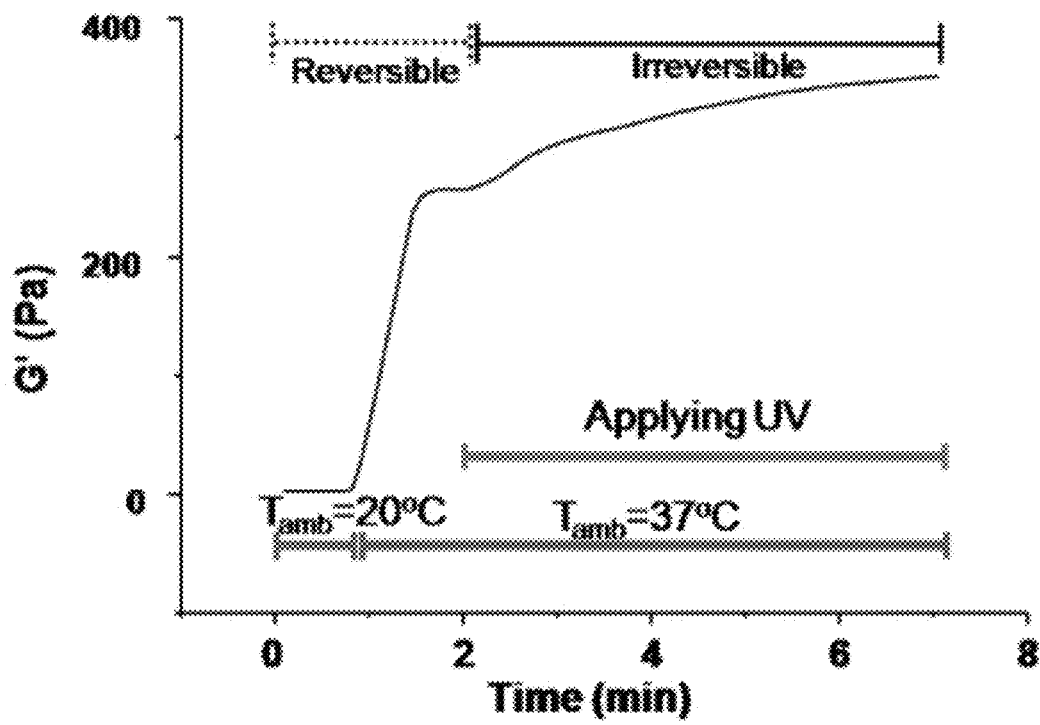
Figure 6:
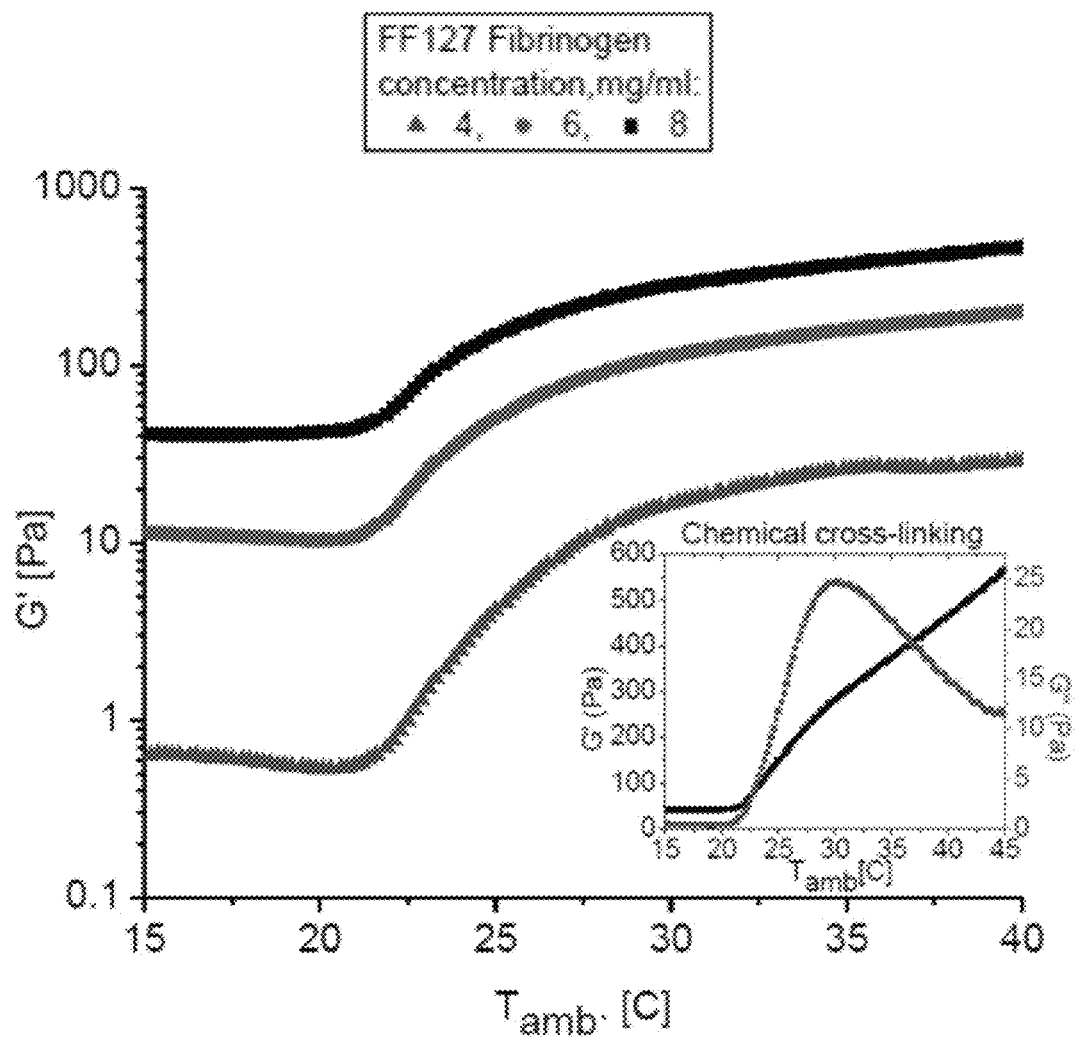
Figures 7A, 7B:
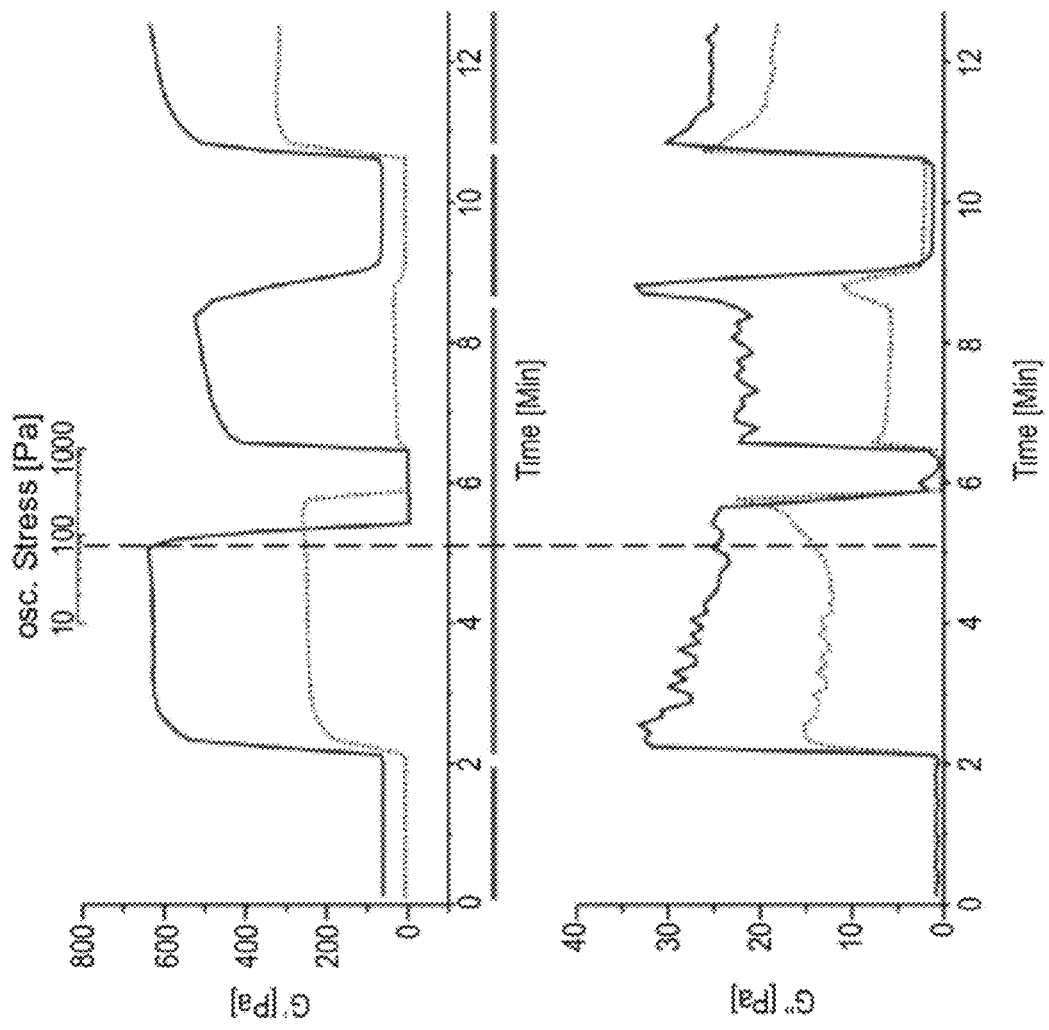
Figure 8:
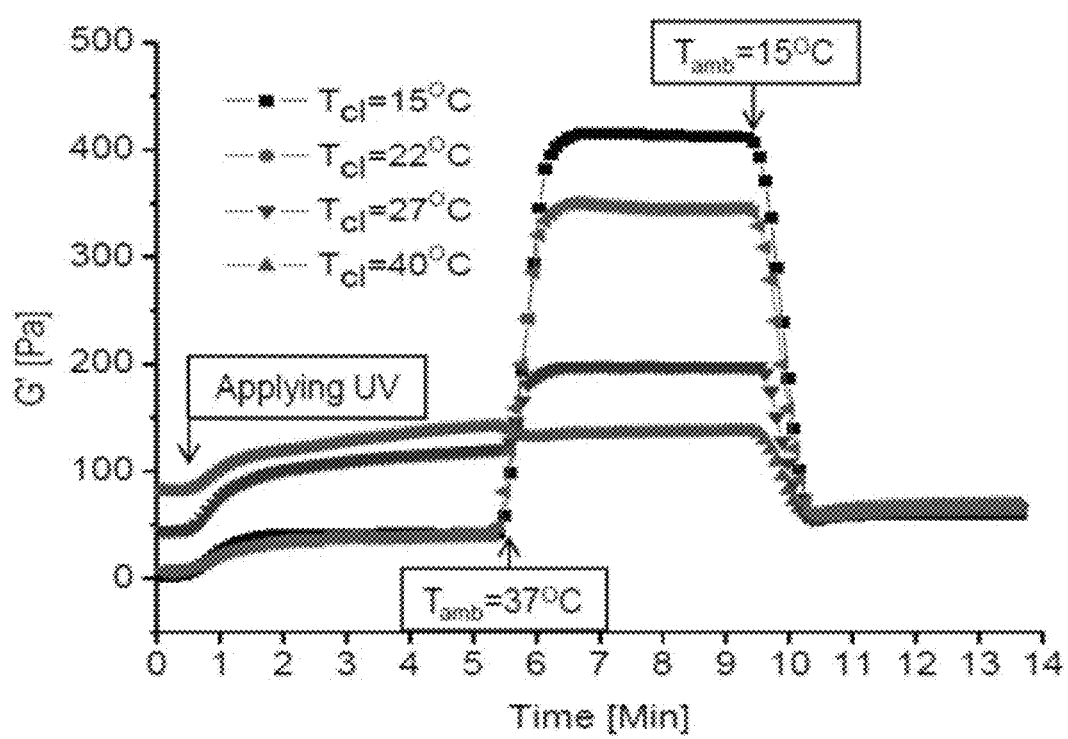
Figure 9:
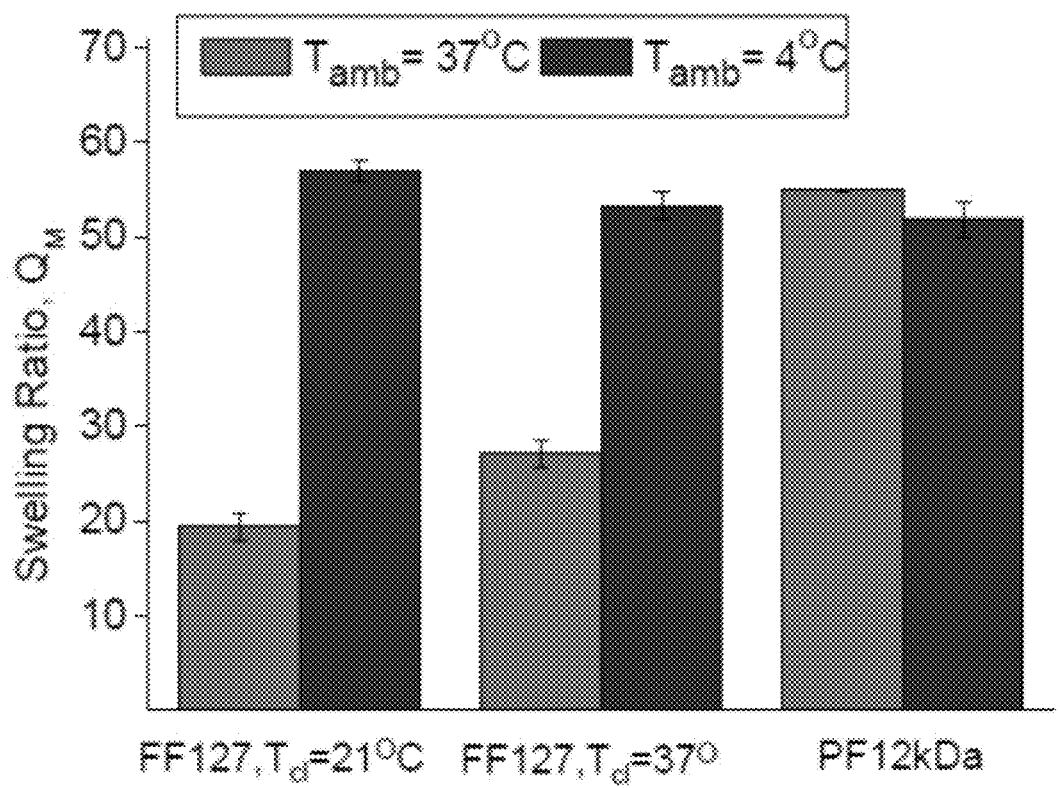
Figure 10A:
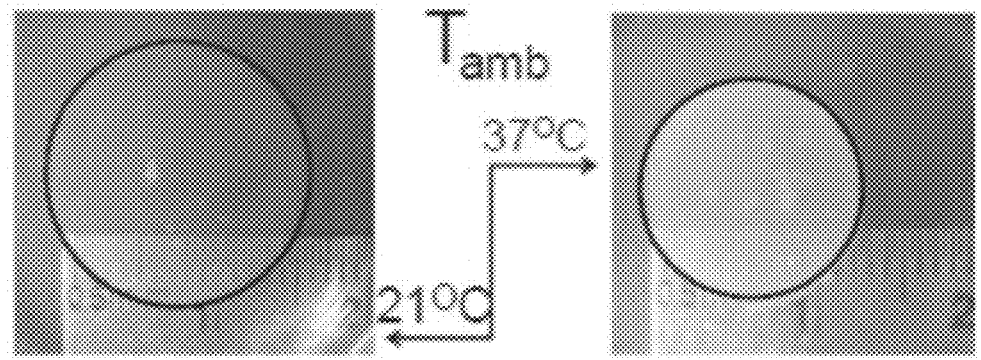
Figure 10B:
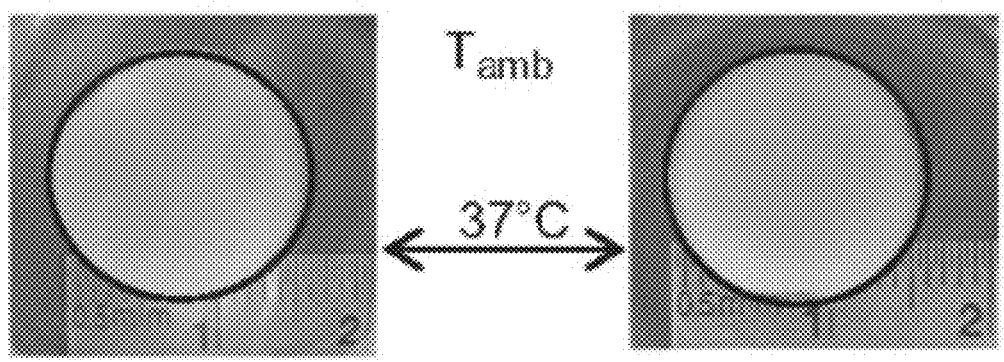
Figure 11:
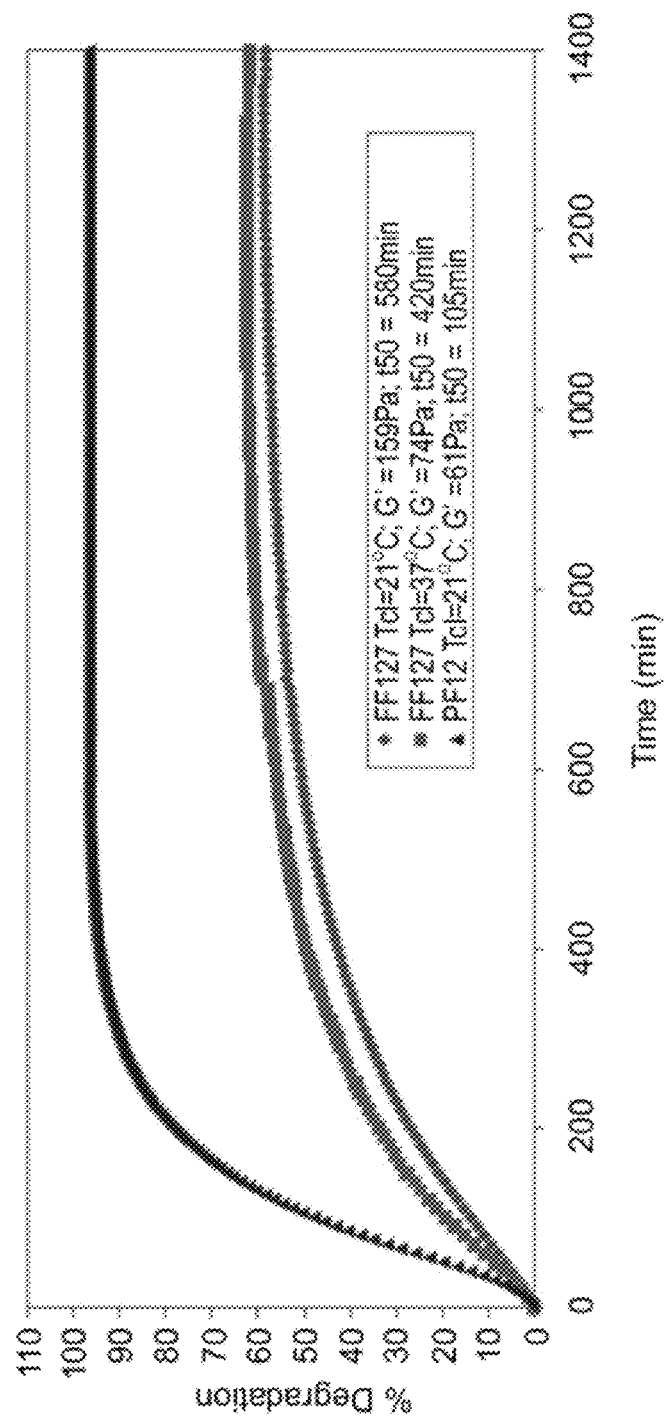
Figure 12:
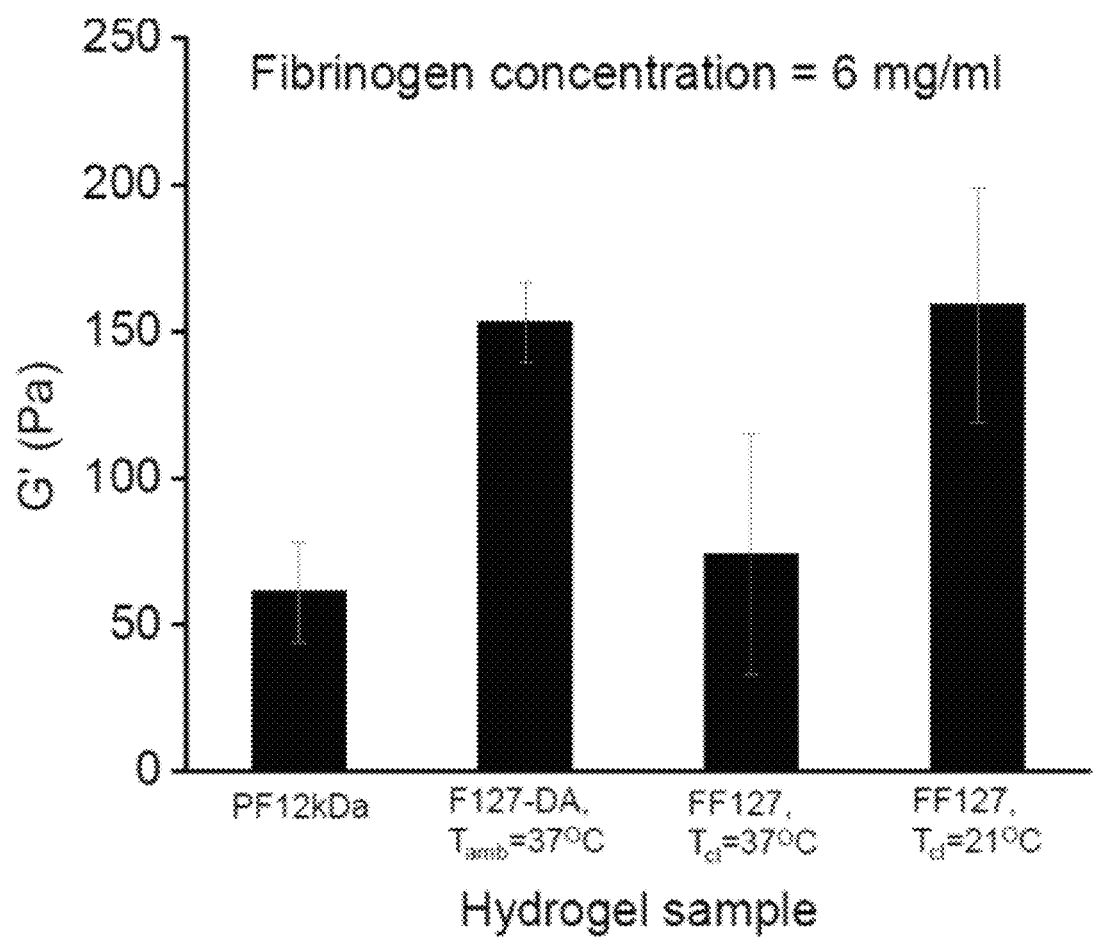
Figure 14A:
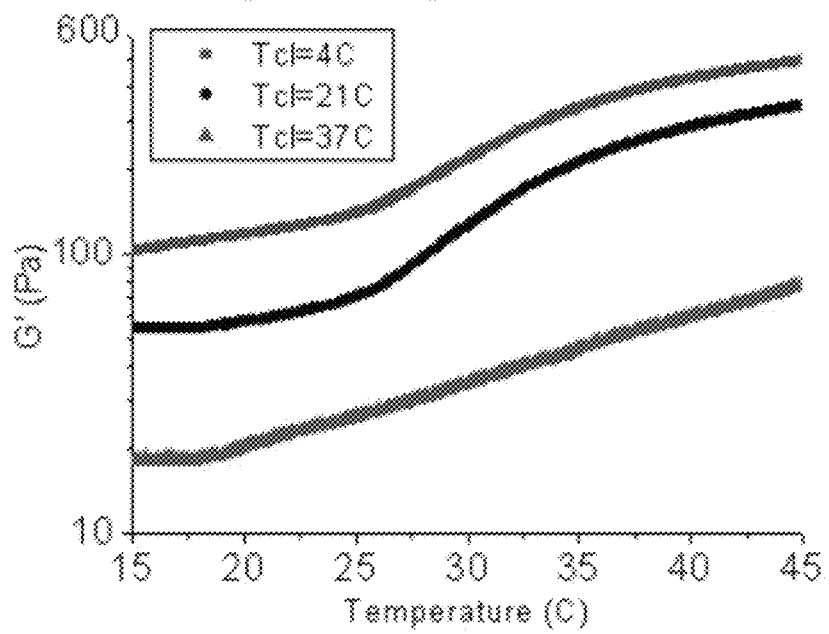
Figure 14B:
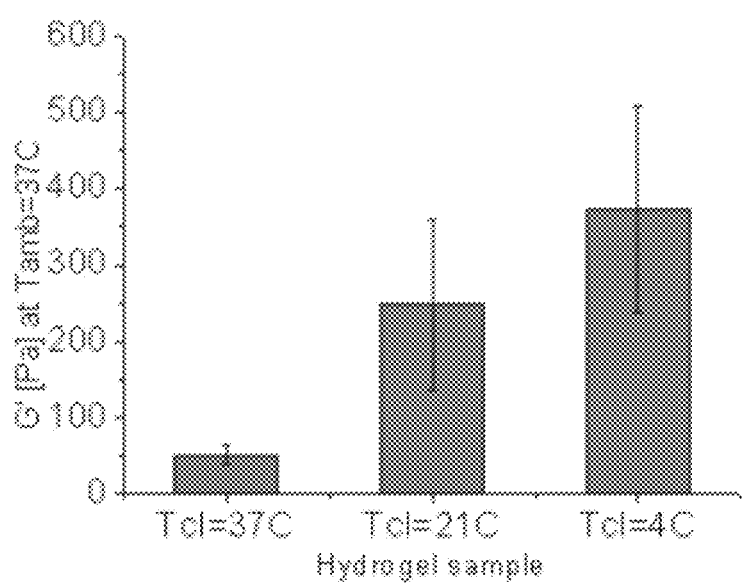
Figure 15:
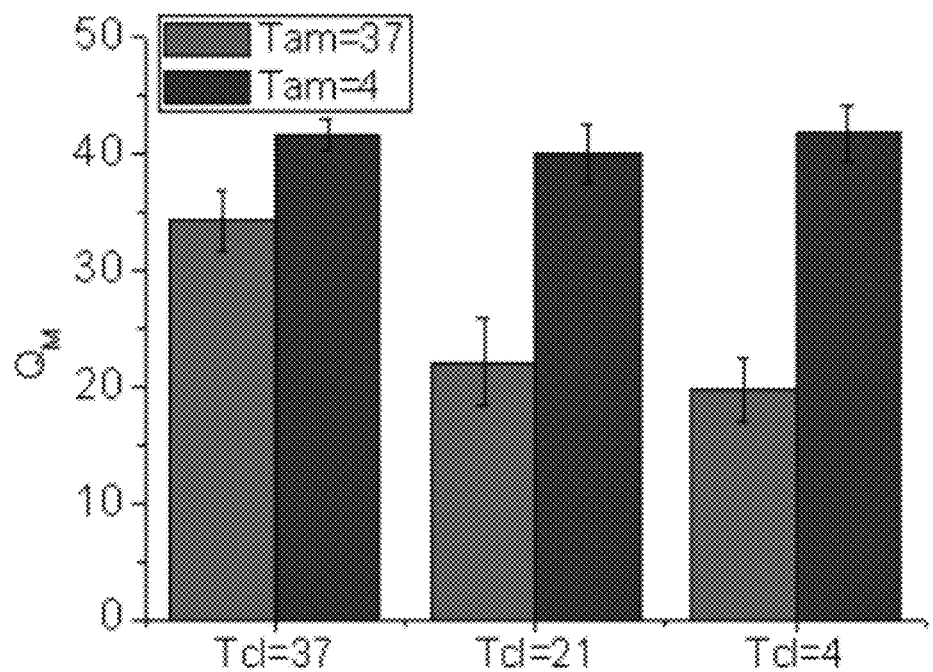
Figure 16:
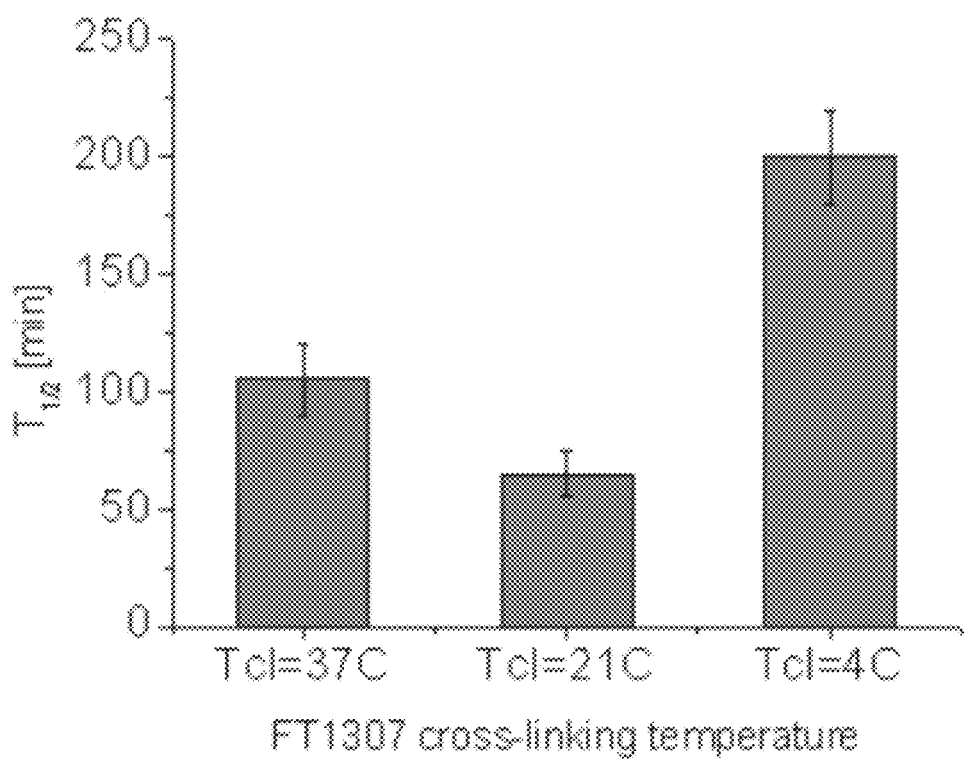
Figure 17:
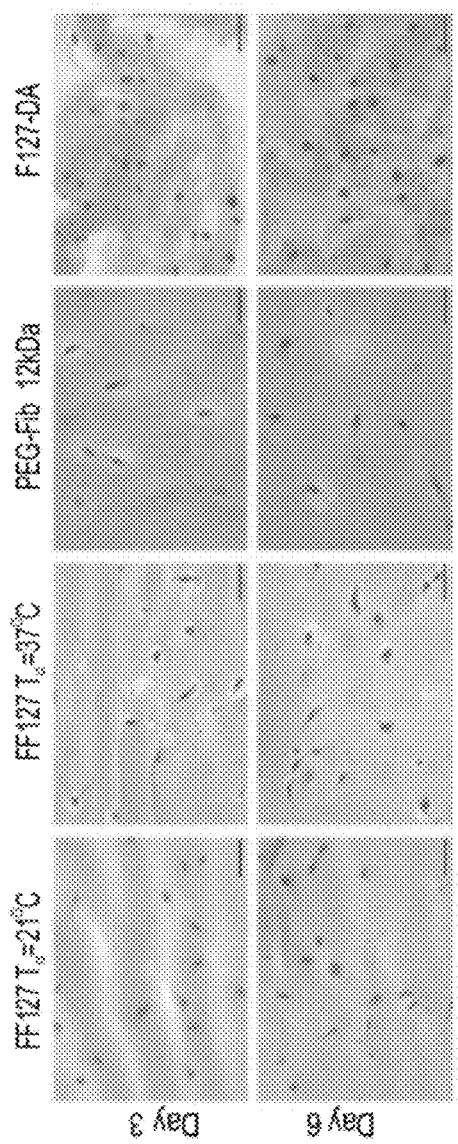
Figure 18:
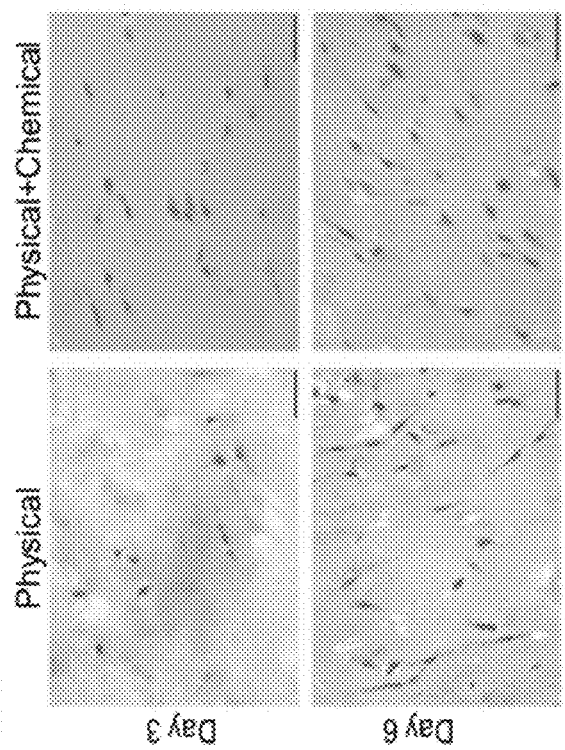
Figure 19:
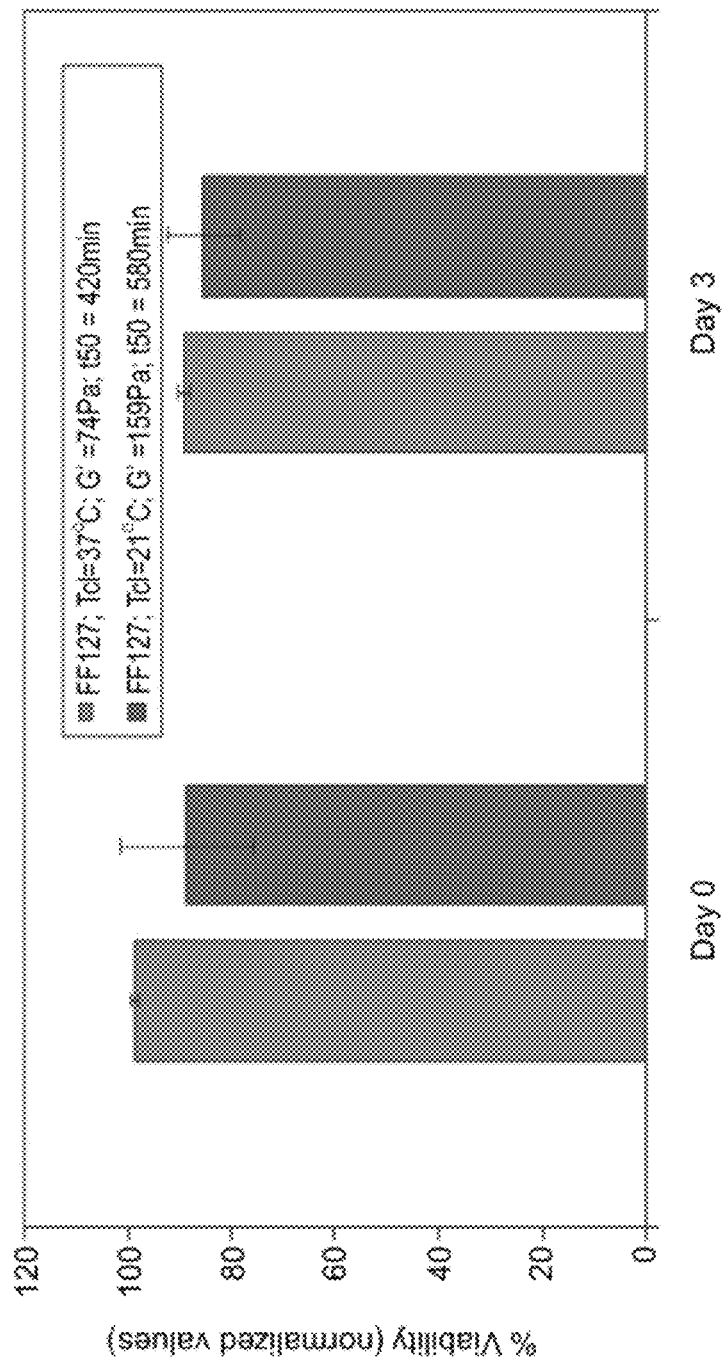
Figure 20A:
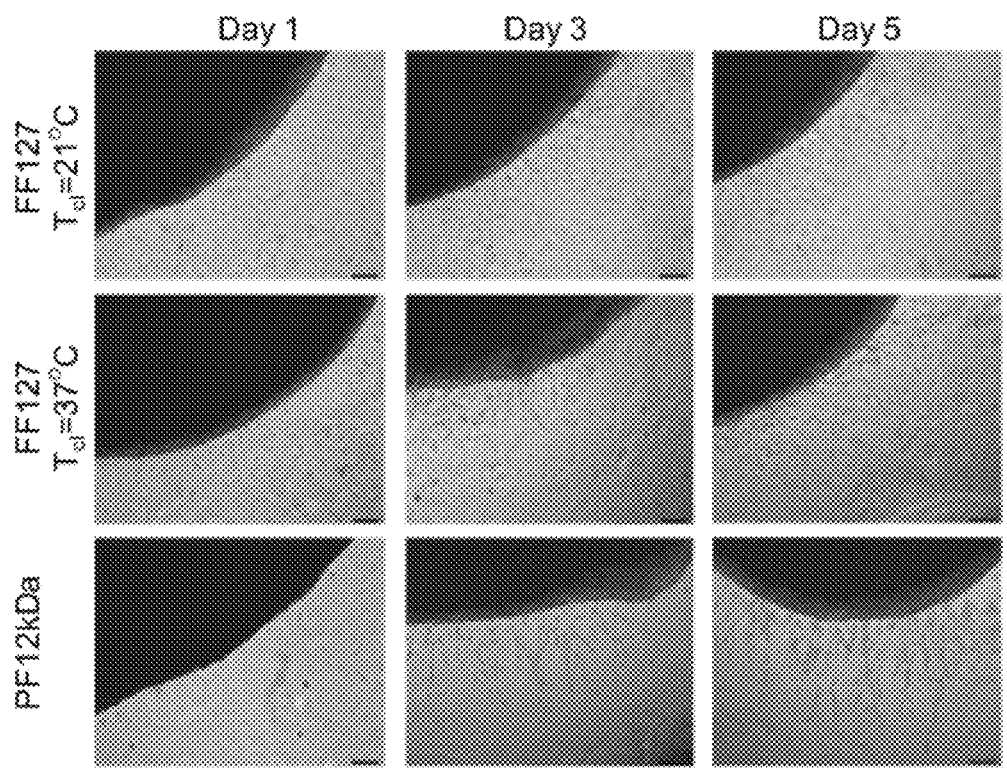
Figure 20B:
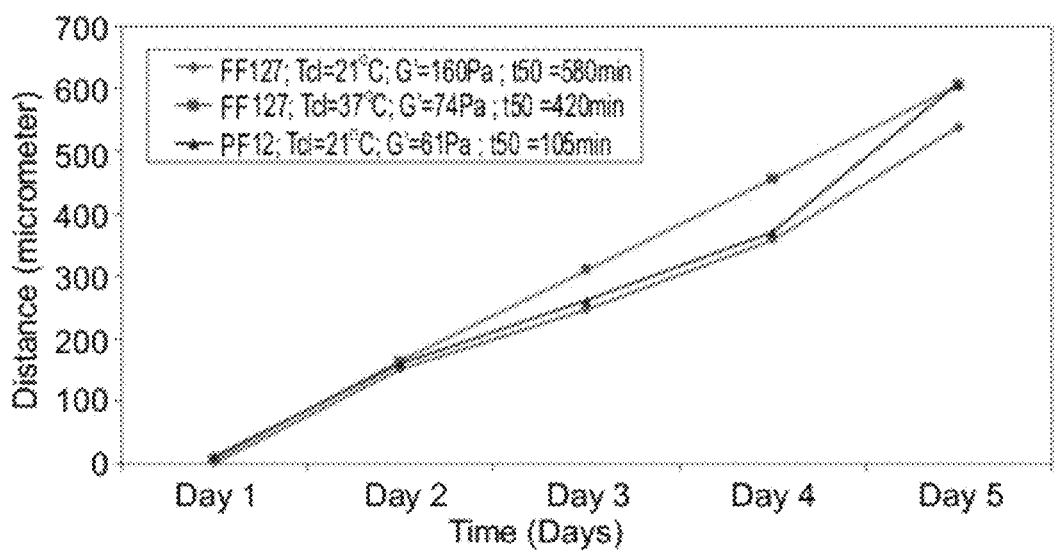
Figure 21:
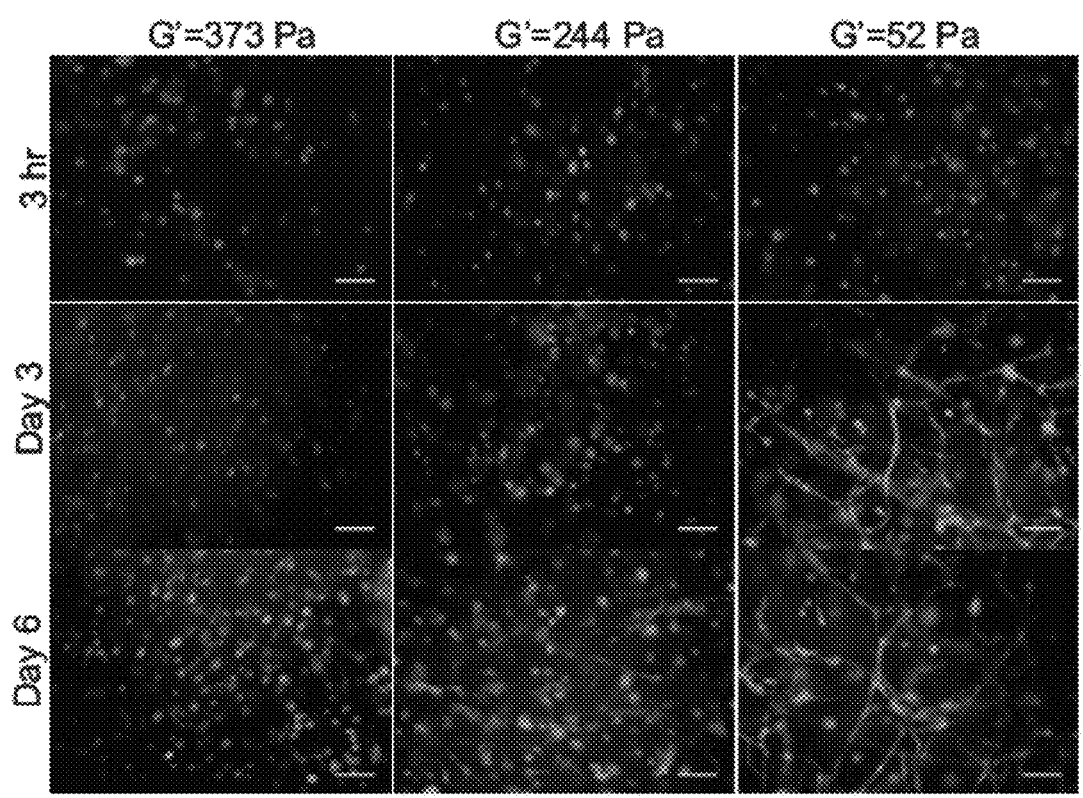
Figure 22:
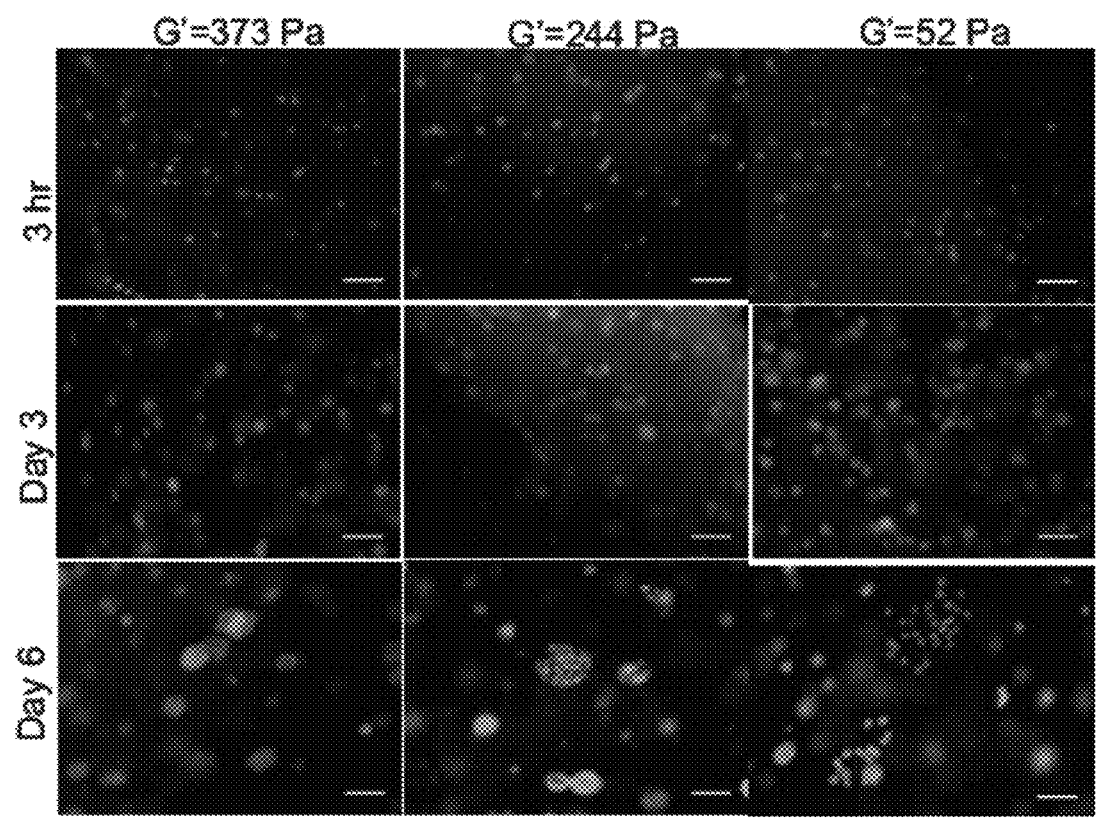
Figure 26A:
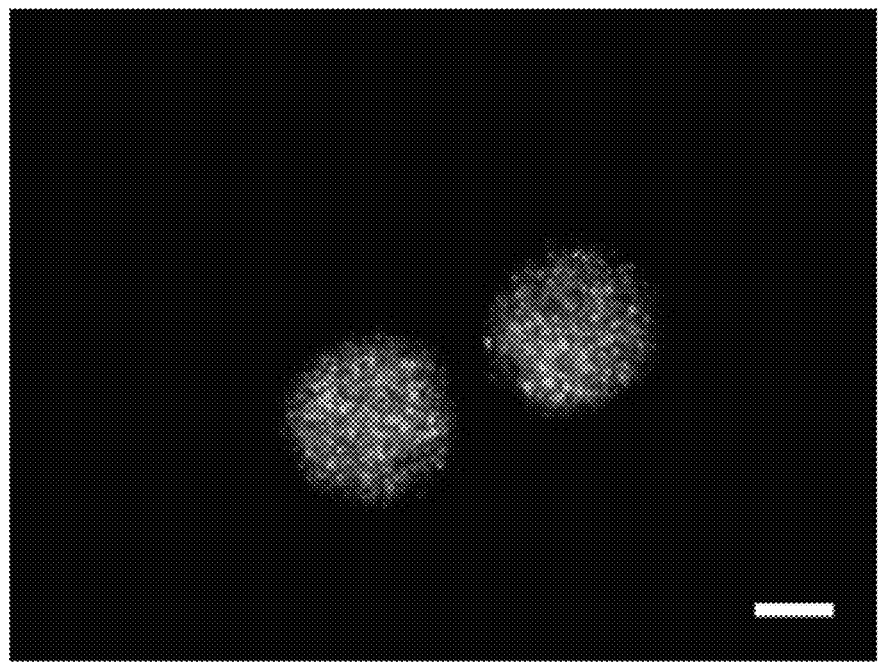
Figure 26B:
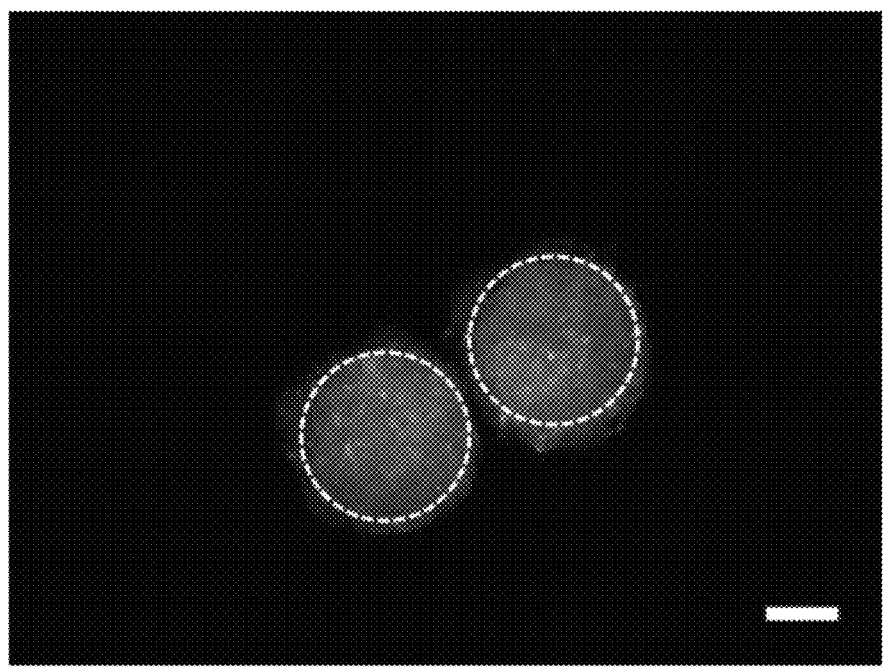
Figure 27A:
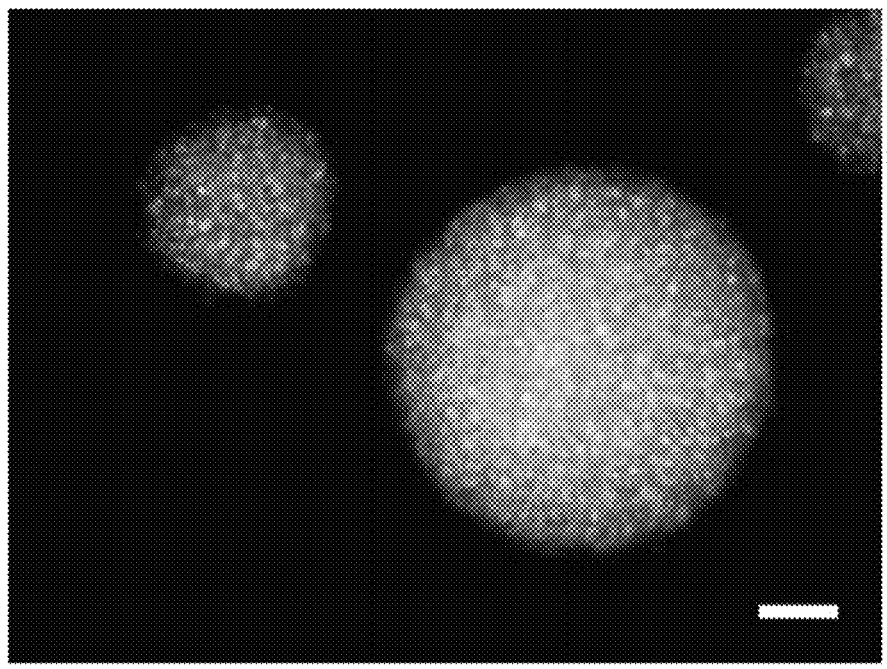
Figure 27B:
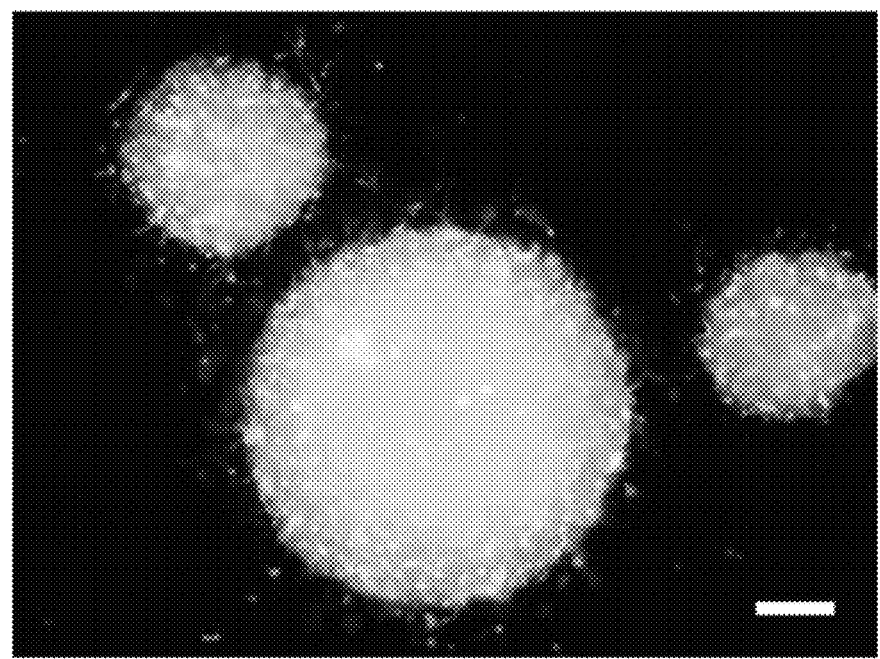

FIGS. 1A and 1B are schemes showing the synthesis of F127 poloxamer diacrylate (FIG. 1A) from F127 poloxamer and acryloyl chloride in a 1:2 mixture of dichloromethane (DCM) and toluene with triethylamine $((ET)_3N)$ at room temperature (R.T.), and the synthesis of an F127 poloxamer-fibrinogen conjugate (FF127) using the poloxamer diacrylate (FIG. 1B) in phosphate buffer saline (PBS) with 8 M urea, according to some embodiments of the invention;

FIG. 2 presents comparative plots showing the storage modulus (G') of FF127 solutions at fibrinogen concentrations of 4, 6 and 8 mg/ml, as a function of temperature; the inset graph shows the storage modulus (G') and loss modulus (G") of an FF127 solution with 8 mg/ml fibrinogen;

FIGS. 3A and 3B present graphs showing the storage moduli of FF127 solutions with (FIG. 3B) and without (FIG. 3A) chemical (covalent) cross-linking of the FF127, as a function of time with cyclic temperature changes between 15° C. and 37° C., in the presence of 0.1 or 0.01 mg/ml collagenase, and in the absence of collagenase;

FIG. 4 is a schematic illustration of fibrinogen polypeptides (red, green and blue) conjugated to a polymer (black) and hydrogel assembly according to some embodiments of the invention by reversible (non-covalent) cross-linking of the polymer in a temperature-dependent manner or irreversible UV-induced (covalent) cross-linking;

FIG. 5 is a graph showing a reversible increase in storage modulus (G') of an FF127 solution by increasing the ambient temperature ($T_{amb}$) and a subsequent irreversible UV-induced increase of the storage modulus;

FIG. 6 presents comparative plots showing the storage modulus (G') of a chemically (covalently) cross-linked FF127 at fibrinogen concentrations of 4, 6 and 8 mg/ml, as a function of temperature; the inset graph shows the storage modulus (G') and loss modulus (G") of a chemically (covalently) cross-linked FF127 with 8 mg/ml fibrinogen;

FIGS. 7A and 7B present graphs showing the effect of oscillatory stress and temperature changes on the storage modulus (G'; FIG. 7A) and loss modulus (G"; FIG. 7B) of hydrogels of 8 mg/ml FF127 with (black line) and without (dotted line) chemical (covalent) cross-linking (temperatures were cycled between 37° C. (red lines) and 15° C. (blue lines) at a rate of 1° C./second; oscillation frequency was 1 Hz; strain was 2%);

FIG. 8 presents a graph showing the storage modulus (G') of FF127 hydrogels (8 mg/ml fibrinogen) cross-linked (covalently) by application of UV light at different cross-linking temperatures ($T_{cl}$), following exposure to ambient temperatures ($T_{amb}$) (before $T_{amb}$=37° C., $T_{amb}$=$T_{cl}$);

FIG. 9 is a bar graph showing the swelling ratio of FF127 hydrogels (6 mg/ml fibrinogen) formed with cross-linking temperatures ($T_{cl}$) of 21° C. or 37° C. and a hydrogel formed from cross-linked 12 kDa PEG-fibrinogen conjugates (PF12 kDa), at ambient temperatures ($T_{amb}$) of 4° C. and 37° C.;

FIGS. 10A and 10B are images showing the diameters (marked by black circles) of FF127 hydrogels (6 mg/ml fibrinogen) chemically (covalently) cross-linked at a temperature of 21° C. (FIG. 10A) or 37° C. (FIG. 10B), and then subjected to ambient temperatures of 37° C.; images on left show the hydrogels at the cross-linking temperature immediately after chemical cross-linking, and images on right show the chemically (covalently) cross-linked hydrogels after incubation at 37° C.;

FIG. 11 presents comparative plots showing the degradation in trypsin solution of hydrogels formed by cross-linking FF127 or 12 kDa PEG-fibrinogen conjugate (PF12) at a cross-linking temperature ($T_{cl}$) of 21° C. or 37° C. (storage moduli (G') and degradation half-lives (t50) of the hydrogels are indicated);

FIG. 12 is a bar graph showing the storage modulus (G') of hydrogels formed by cross-linking FF127 (at a cross-linking temperature ($T_{cl}$) of 21° C. or 37° C.), 12 kDa to PEG-fibrinogen conjugate (PF12 kDa), or F127 diacrylate (F127-DA), at an ambient temperature ($T_{amb}$) of 37° C.;

FIGS. 13A and 13B are schemes illustrating the synthesis (FIG. 13A) of a T1307-fibrinopeptide conjugate (FT-1307) in phosphate buffer saline (PBS) with 8 M urea at room temperature (R.T.), and the structure of the conjugate (FIG. 13B), according to some embodiments of the invention;

FIGS. 14A and 14B present comparative plots (FIG. 14A) and a bar graph (FIG. 14B) showing the storage modulus (G') of FT-1307 (6 mg/ml fibrinogen) hydrogels cross-linked at a temperature ($T_{cl}$) of 4° C., 21° C. or 37° C., as a function of ambient temperature (FIG. 14A), and as a mean±SEM of 4 samples at an ambient temperature of 37° C. (FIG. 14B);

FIG. 15 is a bar graph showing the swelling ratio ($Q_M$) of FT1307 hydrogels (6 mg/ml fibrinogen) cross-linked at a temperature ($T_{cl}$) of 4° C., 21° C. or 37° C., at an ambient temperature ($T_{amb}$) of 4° C. and 37° C.;

FIG. 16 is a bar graph showing the biodegradation half-life ($T_{1/2}$) in trypsin solution of FT1307 hydrogels (6 mg/ml fibrinogen) cross-linked at a temperature ($T_{cl}$) of 4° C., 21° C. or 37° C.;

FIG. 17 presents images showing human foreskin fibroblasts seeded in hydrogels formed by cross-linking FF127 (at a cross-linking temperature ($T_{cl}$) of 21° C. or 37° C.), 12 kDa PEG-fibrinogen conjugate (PEG-Fib 12 kDa), or F127 diacrylate (F127-DA), 3 and 6 days after seeding (scale bar=100 μm);

FIG. 18 is an image showing human foreskin fibroblasts seeded in FF127 hydrogels with (Physical+Chemical) and without (Physical) chemical cross-linking of the FF127 (at a cross-linking temperature of 37° C.), 3 and 6 days after seeding (scale bar=100 μm);

FIG. 19 is a graph showing the viability of human foreskin fibroblasts seeded for 0 or 3 days in hydrogels formed by cross-linking FF127 at a cross-linking temperature ($T_{cl}$) of 21° C. or 37° C. (storage moduli (G') and degradation half-lives (t50) of the hydrogels are indicated);

FIGS. 20A and 20B are an image (FIG. 20A) and a graph (FIG. 20B) showing the cellular invasion from smooth muscle tissue into hydrogels formed by cross-linking FF127 (at a cross-linking temperature ($T_{cl}$) of 21° C. or 37° C.) or 12 kDa PEG-fibrinogen to conjugate (PF12 kDa), on days 1, 3 and 5 after encapsulation of the tissue in the hydrogel; FIG. 20B shows the invasion distance as a function of time (scale bar=100 μm);

FIG. 21 is an image showing human foreskin fibroblasts 3 hours, 3 days or 6 days after being seeded in FT1307 hydrogels with storage moduli of 52, 244 or 373 Pa (viable cells are stained with calcein (green) and non viable cells are stained with ethidium (orange); scale bar=100 μm);

FIG. 22 is an image showing HeLa cells 3 hours, 3 days or 6 days after being seeded in FT1307 hydrogels with storage moduli of 52, 244 or 373 Pa (viable cells are stained with calcein (green) and non viable cells are stained with ethidium (orange); scale bar=100 μm);

FIGS. 23A and 23B depict the preparation of a cell-seeded FF127 capsule embedded in an FT1307 hydrogel, according to some embodiments of the invention;

FIGS. 24A and 24B are photographs showing an FF127 capsule (6 mg/ml fibrinogen) seeded with human foreskin fibroblasts (green) embedded for 6 days in an FT1307 hydrogel (6 mg/ml fibrinogen) having a storage modulus of 373 Pa (FIG. 24A) or 52 Pa (FIG. 24B) (scale bar=200 μm);

FIGS. 25A and 25B are photographs showing an FF127 capsule (6 mg/ml fibrinogen) seeded with Hela cells (green) embedded for 6 days in an FT1307 hydrogel (6 mg/ml fibrinogen) having a storage modulus of 373 Pa (FIG. 25A) or 52 Pa (FIG. 25B) (scale bar=200 μm);

FIGS. 26A and 26B are photographs showing FF127 capsules (6 mg/ml fibrinogen) seeded with a co-culture of human foreskin fibroblasts (stained green) and Hela cells (stained red) on day 0 (FIG. 26A) and on day 5 (FIG. 26B) of being embedded in an FT1307 hydrogel (6 mg/ml fibrinogen) (dashed circles in FIG. 26B show the diameter of the cell culture on day 0, scale bar=200 μm); and FIGS. 27A and 27B are photographs showing FF127 capsules (6 mg/ml fibrinogen) seeded with a co-culture of human foreskin fibroblasts (stained green) and Hela cells (stained red) on day 0 (FIG. 26A) and on day 5 (FIG. 26B) of being embedded in an FT1307 hydrogel (6 mg/ml fibrinogen) (scale bar=200 μm).

DESCRIPTION OF SPECIFIC EMBODIMENTS OF THE INVENTION

The present invention, in some embodiments thereof, relates to polymer-protein conjugates and, more particularly, but not exclusively, to polymer-protein conjugates which form a scaffold, to processes of generating same and to uses thereof in, for example, tissue engineering.

The conjugation of a synthetic polymer to a natural protein such as fibrinogen provides a means of creating biocompatible hydrogels while controlling their physical properties. The conjugation reaction is intended to endow the protein constituent with additional structural versatility, without compromising its biocompatibility.

The present inventors have previously disclosed a methodology of generating hydrogels made from a synthetic polymer such as poly(ethylene glycol) (PEG) conjugated to fibrinogen, which enables to control cellular behavior of the formed hydrogels by manipulating factors such as density, stiffness, and proteolytic degradability through the versatile synthetic component.

In a search for methodologies for generating hydrogels with improved control of the hydrogel's characteristics, the present inventors have designed and successfully practiced a methodology of generating "smart" hydrogels, by conjugating to proteins a synthetic polymer that exhibits a reverse thermal gelation (RTG) property above a critical temperature in aqueous solutions.

This methodology was found to produce hydrogels with an exceptional control of physical characteristics of the hydrogels, since it allows manipulating these characteristics by selecting, for example, the degree and nature of the cross-linking reactions that lead to gel formation. Since it was uncovered that the protein-polymer conjugates exhibit a reverse thermal gelation property, the degree and occurrence of non-covalent (physical) cross-linking can be controlled, whereby chemical conditions can be selected for effecting covalent cross-linking if desired.

Thus, using a combination of photo-polymerization cross-linking and temperature, an exceptional control over physical properties of the generated hydrogels was demonstrated. The ability of the generated hydrogels to act as a matrix for cell and tissue growth and survival (e.g., as a scaffold) has also been demonstrated.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The present inventors have demonstrated the novel methodology while utilizing Pluronic® F127 poloxamer and Tetronic® T1307 copolymer (a poloxamer derivative) which are end-functionalized with acryl groups and are reacted with denatured fibrinogen via a Michael-type addition reaction to form a protein-copolymer conjugate. These exemplary polymeric conjugates could cross-link to form a structure comprising multiple units ("unimers") of the conjugate. Rheological measurements were conducted on the functionalized unimers and the hydrogels generated therefrom in order to characterize the physical response of these conjugates to environmental stimuli (e.g., temperature responsiveness).

The present inventors have thus further uncovered that the generated hydrogels retain the biocompatibility of their fibrinogen constituent with the added advantage of enhanced precision in controlling the physical properties of the polymeric network using the synthetic F127 constituent.

It was shown that the conjugation reaction does not eliminate the self-assembly properties of the F127, but rather enhances it, thus endowing the obtained protein-polymer conjugates with reverse thermal gelation (RTG) properties. Thus, it was uncovered that the poloxamer-fibrinogen conjugate surprisingly undergoes gelation at low concentrations (e.g., below 20 mg/ml conjugate), which are considerably lower than the concentrations necessary for reverse thermal gelation of the poloxamer alone. This indicates that the protein acts as a chain extender that allows the poloxamer-protein conjugate to undergo gelation at these exceptionally lower concentrations.

The ability to obtain hydrogels at low conjugate concentrations is advantageous for applications such as tissue regeneration, because such hydrogels are better suited for allowing cell growth and migration within a hydrogel.

Using a combination of photo-polymerization cross-linking and temperature, an exceptional control over physical properties of the generated hydrogels was demonstrated. The ability of the generated hydrogels to act as a matrix for cell and tissue growth and survival has also been demonstrated.

Referring now to the drawings, FIGS. 1A and 1B illustrate the synthesis of an exemplary F127 poloxamer-fibrinogen conjugate.

FIG. 2 shows the gelation of the conjugate by an increase of temperature (i.e., reverse thermal gelation) at various concentrations, including at conjugate concentrations below 20 mg/ml. Such concentrations are lower than the concentrations that allow reverse thermal gelation of F127 poloxamer alone, indicating that conjugation to fibrinogen enhanced the RTG properties of the poloxamer by acting as a chain extender.

FIGS. 3A and 3B show that the reverse thermal gelation of the conjugate is reversible, such that gelation can be repeatedly induced and reversed, even after the conjugate has been covalently cross-linked (FIG. 3B). FIG. 6 shows the reverse thermal gelation of covalently cross-linked conjugate at various concentrations.

FIG. 4 illustrates two types of cross-linking which molecules of the conjugate can undergo to form a hydrogel; a reversible temperature-dependent cross-linking of conjugate molecules (by reverse thermal gelation), and an irreversible cross-linking induced by UV light. FIG. 5 shows increases in shear storage modulus resulting from both reversible and irreversible cross-linking of conjugate molecules.

FIGS. 7A and 7B show the different behaviors of exemplary covalently cross-linked and non-covalently cross-linked hydrogels in response to stress. FIGS. 7A and 7B also show that after collapsing in response to stress, both types of hydrogel recover completely after lowering and increasing the temperature so as to undo and restore the reverse thermal gelation.

FIGS. 8 and 12 show that the shear storage modulus of exemplary covalently cross-linked hydrogels depends strongly on the temperature at which the conjugate is covalently cross-linked. FIG. 11 shows that the effect of cross-linking temperature on biodegradability is considerably weaker, and that biodegradability is affected more by the type of polymer conjugated to the protein.

FIGS. 9-10B show that the swelling properties of covalently cross-linked poloxamer-fibrinogen hydrogels are temperature-dependent (in contrast to cross-linked PEG-fibrinogen hydrogels), and that the degree of temperature dependency is affected by the cross-linking temperature.

FIGS. 13A and 13B illustrate the synthesis of an exemplary T1307-fibrinogen conjugate, wherein each T1307 moiety in the conjugate comprises three acrylate cross-linking moieties.

FIGS. 14A and 14B show that the shear storage modulus of covalently cross-linked T1307-fibrinogen hydrogels depends strongly on the temperature at which the conjugate is covalently cross-linked. FIG. 15 shows that the swelling properties of covalently cross-linked T1307-fibrinogen hydrogels are temperature-dependent, and that the degree of temperature dependency is affected by the cross-linking temperature.

FIG. 16 shows that that biodegradability is not clearly correlated with the cross-linking temperature.

The results presented in FIGS. 14A-16 indicate that the properties of T1307-containing hydrogels are similar to those of F127 poloxamer-containing hydrogels.

FIGS. 17-22 and 24A-27B show that exemplary hydrogels can serve as matrices for cell growth and invasion, and that the rate and type of cellular growth and invasion depends on the covalent cross-linking temperature of the hydrogels. FIGS. 26A-27B show the effects of different hydrogel properties on cell growth in a co-culture of different cell types.

FIGS. 23A and 23B illustrate an exemplary process for preparing a hydrogel capsule with one set of physical properties, embedded within a hydrogel with a different set of physical properties.

Thus, it has been demonstrated that polymer-fibrinogen conjugates according to exemplary embodiments of the invention can be readily cross-linked so as to form hydrogel scaffolds. In addition, non-covalent and covalent cross-linking can be readily combined. The hydrogels exhibit high flexibility, biodegradability, good biofunctionality and support for cell spreading and invasion, and a shear storage modulus which can be readily controlled by various parameters. The temperature at which covalent cross-linking is performed was particularly useful for controlling the shear storage modulus, as it has relatively little effect on other properties, such as biodegradability.

According to one aspect of the present invention, there is provided a conjugate comprising a polypeptide having attached thereto at least two polymeric moieties, at least one of the polymeric moieties exhibiting a reverse thermal gelation. In some embodiments, each of the polymeric moieties exhibits a reverse thermal gelation.

As used herein, the phrase "reverse thermal gelation" describes a property whereby a substance (e.g., an aqueous solution of a compound) increases in viscosity upon an increase in temperature. The increase in viscosity may be, for example, conversion from a liquid state to a semisolid state (e.g., gel), conversion from a liquid state to a more viscous liquid state, or conversion from a semisolid state to a more rigid semisolid state. Herein, all such conversions are encompassed by the term "gelation". The increase in temperature which effects gelation may be between any two temperatures. Optionally, the gelation is effected at a temperature within the range of 0° C. to 55° C.

Herein, a polymeric moiety is considered to exhibit a reverse thermal gelation when an aqueous solution of a polymer which corresponds to the polymeric moiety (e.g., a polymer not attached to the abovementioned polypeptide) exhibits a reverse thermal gelation, as described herein.

A variety of polymers exhibit a reverse thermal gelation. Each polymer may be characterized by a critical gelation temperature, wherein gelation is effected at the critical gelation temperature or at temperatures above the critical gelation temperature.

Herein, "critical gelation temperature" refers to the lowest temperature at which some gelation of a material is observed (e.g., by increase in shear storage modulus).

The polymeric moiety may be selected so as to impart to the conjugate containing same a reverse thermal gelation that is characterized by a critical gelation temperature within a temperature range (e.g., in a range of 0° C. to 55° C.) which allows for convenient manipulation of the properties of the conjugate by exposure to an ambient temperature above and/or below the critical gelation temperature.

The critical gelation temperature of the polymer may be selected, for example, based on the intended use or desired properties of a conjugate. For example, the critical gelation temperature may be selected such that the conjugate is in a gelled state at a physiological temperature but not at room temperature, such that gelation may be effected in vivo. In another example, the critical gelation temperature may be selected such that the conjugate is in a gelled state at room temperature but not at a moderately lower temperature, such that gelation may be effected, for example, by removal from refrigeration.

The polymeric moiety optionally comprises a synthetic polymer. Poloxamers (e.g., F127 poloxamer) are exemplary polymers which exhibit a reverse thermal gelation at temperatures suitable for embodiments of the present invention.

As used herein and in the art, a "poloxamer" refers to poly(ethylene oxide) (PEO)-poly(propylene oxide) (PPO) block copolymer having a PEO-PPO-PEO structure. Suitable poloxamers are commercially available, for example, as Pluronic® polymers.

Typically, reverse thermal gelation is mediated by the formation of non-covalent cross-linking (e.g., via hydrophobic interactions, ionic interactions, and/or hydrogen bonding) between molecules, wherein the degree of non-covalent cross-linking increases in response to an increase of temperature.

Herein, "non-covalent" cross-linking (formed as a result of a reverse thermal gelation) is also referred to as "physical" cross-linking or as "non-chemical cross-linking". The non-covalent cross-linking can therefore be understood as a temperature-dependent cross-linking.

The polymeric moiety may comprise one or more moieties which effect non-covalent cross-linking (e.g., hydrophobic moieties). The degree of gelation and the conditions (e.g., temperature) under which gelation is effected may optionally be controlled by the nature and the number of moieties which participate in non-covalent cross-linking.

The polymeric moiety may comprise from 1 and up to 100 and even 1000 moieties which participate in non-covalent cross-linking. In many embodiments, the higher the number of such moieties, and the larger the moieties are (e.g., the higher the molecular weights are), the lower the temperature under which gelation is effected.

The polymeric moiety may comprise one or more types of moieties which effect cross-linking. These moieties may effect non-covalent cross-linking via the same intermolecular interactions (e.g., hydrophpbic interactions) or via different intermolecular interactions (e.g., hydrophobic and ionic interactions). Polymers that exhibit reverse thermal gelation (also referred to in the art as RTG polymers) include, but are not limited to, poly(N-isopropylacrylamide), which undergoes reverse thermal gelation at temperatures above about 32-33° C., as well as copolymers thereof (e.g., poly(N-isopropylacrylamide-co-dimethyl-γ-butyrolactone), poly(ethylene glycol)-poly(amino urethane) (PEG-PAU) block copolymers, poly(ε-caprolactone)-poly(ethylene glycol) (PCL-PEG) block copolymers (e.g., PCL-PEG-PCL), and poly (methyl 2-propionamidoacrylate). In addition, polyorganophosphazenes with PEG and hydrophobic oligopeptide side groups (which provide intermolecular hydrophobic interactions) have been described, which are gelled at temperatures of 35-43° C. [Seong et al., *Polymer* 2005, 46:5075-5081].

For example, a poloxamer moiety comprises a hydrophobic PPO moiety which mediates gelation. A polymeric moiety may optionally comprise one such PPO moiety, or alternatively, a plurality (e.g., 2, 3, 4, etc., up to 100 and even 1000 such moieties) of such moieties.

Similarly PCL-PEG copolymers comprise hydrophilic PEG and a relatively hydrophobic poly(ε-caprolactone) (PCL) moiety, and PEG-PAU copolymers comprise hydrophilic PEG and a hydrophobic poly(amino urethane) (PAU) moiety (e.g., a bis-1,4-(hydroxyethyl)piperazine-1,6-diisocyanato hexamethylene condensation polymer moiety).

Thus, in general, many block polymers exhibiting reverse thermal gelation may be prepared from a combination of hydrophilic and hydrophobic building blocks.

In some embodiments, each polymeric moiety comprises a poloxamer (e.g., F127 poloxamer).

Optionally, a polymeric moiety comprises one poloxamer.

Alternatively or additionally, at least one polymeric moiety comprises a plurality of poloxamer moieties. Polymers comprising a plurality of poloxamer moieties are commercially available, for example, as Tetronic® polymers. T1307 (e.g., Tetronic® T1307) is an exemplary polymer which comprises four poloxamer moieties.

According to optional embodiments, at least one of the polymeric moieties further comprises at least one cross-linking moiety for covalently cross-linking a plurality of molecules of the conjugate to one another. Optionally, the polymeric moiety comprises from 1 to 10, optionally from 1 to 5, and optionally from 1 to 3 cross-linking moieties.

It to be noted that the expression "cross-linking moiety" is used herein to describe moieties that are attached to the polymeric moiety (e.g., as an end group or as pendant groups), or which form an integral part of the polymeric moiety, yet it differs from those moieties in the polymeric moiety that effect non-covalent cross-linking, as described hereinabove.

A "cross-linking moiety" as used herein thus describes moieties on the polymeric moiety that effect covalent cross-linking, as defined herein, between molecules of the conjugate.

Herein, "covalent cross-linking" (also referred to herein as "chemical cross-linking") refers to a formation of a covalent bond ("cross-link") between two or more molecules (e.g., two conjugate molecules described herein). A molecule may be attached to a plurality of other molecules, each other molecule being attached by a different covalent bond. Thus, a plurality of molecules (e.g., at least 5, at least 10, at least 20, at least 50, at least 100) may be linked together.

A conjugate as described may optionally be represented by the general formula:

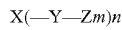

X(—Y—Z$m$)$n$ wherein X is a polypeptide as described herein, Y is a polymeric moiety as described herein, Z is a cross-linking moiety as described herein, n is an integer greater than 1 (e.g., 2, 3, 4 and up to 20), and m represents the number of cross-linking moieties per polymeric moiety. Thus, m is 0 in embodiments lacking the optional cross-linking moiety, and m is 1 or an integer greater than 1, in embodiments which comprise the optional cross-linking moiety.

It is to be understood that as the above formula includes more than one —Y—Z$m$ moiety, different —Y—Z$m$ moieties in a conjugate may optionally have a different values for m.

As used herein, the phrase "cross-linking moiety" refers to a moiety (e.g., a functional group) characterized by an ability to effect covalent cross-linking with a functional group of another molecule (e.g., another conjugate).

According to optional embodiments, the cross-linking moiety is able to effect cross-linking with a conjugate similar to and/or identical to the conjugate described herein (e.g., a conjugate comprising a cross-linking moiety chemically related to and/or identical to the cross-linking moiety of the conjugate described herein).

Thus, the cross-linking moiety described herein provides a conjugate with an ability to undergo covalent cross-linking, whereas a polymeric moiety which exhibits reverse thermal gelation, as described herein, provides a conjugate with an ability to undergo non-covalent cross-linking (self-assembly). Hence, in embodiments without a cross-linking moiety (e.g., wherein m in the general formula is 0), cross-linking of the conjugate may be effected solely by non-covalent cross-linking by the polymeric moiety, whereas in embodiments with a cross-linking moiety (e.g., wherein m in the general formula is 1 or more), cross-linking of the conjugate may be effected by non-covalent cross-linking and/or by covalent cross-linking, as discussed in more detail herein.

Exemplary cross-linking moieties that are suitable for use in the context of embodiments of the invention include, but are not limited to, polymerizable groups, as further detailed hereinbelow.

Thus, in some embodiments, the cross-linking moiety comprises a polymerizable group, such that cross-linking may be effected by polymerization of the polymerizable group. In the context of embodiments of the present invention, the polymerizable groups may act as monomers, whereby polymerization of the polymerizable groups cross-links the conjugates comprising the polymerizable groups.

Many polymerizable groups are known in the art, including groups (e.g., unsaturated groups) which readily undergo free radical polymerization, and cyclic groups (e.g., lactones) which readily undergo polymerization via ring-opening. Polymerization can be effected, for example, via photoinitiation (in the presence of an appropriate light, e.g., 365 nm), via chemical cross-linking (in the presence of a free-radical donor) and/or heating (at the appropriate temperatures).

In some embodiments, a polymerizable group is selected such that polymerization thereof may be effected under relatively mild conditions which are non-harmful to living cells. For example, the polymerization conditions are optionally sufficiently non-toxic and non-hazardous so as to be suitable for effecting polymerization in vivo, as described herein.

It is to be noted that covalent cross-linking can be effected also in presence of a cross-linking agent. Such an agent is typically a bifunctional chemical moiety that is capable of reacting with the cross-linking group. Examples include, but are not limited to, PEGs terminated at both ends with a reactive group that can readily react with the cross-linking group.

In some embodiments, the polymerizable group is polymerizable by free radical to polymerization. Examples of such groups include, without limitation, an acrylate, a methacrylate, an acrylamide, a methacrylamide, and a vinyl sulfone.

According to optional embodiments, the conjugate comprises polymeric moiety which comprise a plurality cross-linking moieties which can attach to a polypeptide. For example, acrylate, methacrylate, acrylamide, methacrylamide, and vinyl sulfone, in addition to being polymerizable groups, are suitable for attachment to a thiol group (e.g., in a cysteine residue) via Michael-type addition.

Thus, as exemplified in the Examples section herein, a polymeric moiety may comprise a plurality of such moieties (e.g., acrylate), one of which attached the polymeric moiety to the polypeptide, the remaining moieties being cross-linking moieties as described herein.

Thus, in exemplary embodiments, the conjugate comprises poloxamer diacrylate (e.g., F127 poloxamer diacrylate) moieties, wherein one acrylate group in each moiety is attached to a cysteine residue of a polypeptide (e.g., denatured fibrinogen), and one acrylate group serves as a cross-linking moiety.

In additional exemplary embodiments, the conjugate comprises a polymeric tetraacrylate (e.g., T1307 tetraacrylate) moieties, wherein one acrylate group in each moiety is attached to a cysteine residue of a polypeptide (e.g., denatured fibrinogen), and three acrylate groups serve as cross-linking moieties.

The polypeptide of the conjugate is at least 10 amino acids in length, optionally at least 20 amino acids in length, and optionally at least 50 amino acids in length.

The term "polypeptide" as used herein encompasses native polypeptides (either degradation products, synthetically synthesized polypeptides or recombinant polypeptides) and peptidomimetics (typically, synthetically synthesized polypeptides), as well as peptoids and semipeptoids which are polypeptide analogs, which may have, for example, modifications rendering the polypeptides more stable while in a body or more capable of penetrating into cells. Such modifications include, but are not limited to, N-terminus modification, C-terminus modification, peptide bond modification, including, but not limited to, $CH_2$—NH, $CH_2$—S, $CH_2$—S=O, O=C—NH, $CH_2$—O, $CH_2$—$CH_2$, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

Peptide bonds (—CO—NH—) within the peptide may be substituted, for example, by N-methylated bonds (—N($CH_3$)—CO—), ester bonds (—C(R)H—C—O—O—C(R)—N—), ketomethylen bonds (—CO—$CH_2$—), -aza bonds (—NH—N(R)—CO—), wherein R is any alkyl, e.g., methyl, carba bonds (—$CH_2$—NH—), hydroxyethylene bonds (—CH(OH)—$CH_2$—), thioamide bonds (—CS—NH—), olefinic double bonds (—CH=CH—), retro amide bonds (—NH—CO—), peptide derivatives (—N(R)—$CH_2$—CO—), wherein R is the "normal" side chain, naturally presented on the carbon atom. These modifications can occur at any of the bonds along the polypeptide chain and even at several (2-3) at the same time.

As used herein throughout, the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

According to optional embodiments, the polypeptide comprises a protein or a fragment thereof.

The protein may be a naturally occurring protein (e.g., a protein existing in eukaryotic and/or prokaryotic organisms, cells, cellular material, non-cellular material, and the like) or a polypeptide homologous (e.g., at least 90% homologous, optionally at least 95% homologous, and optionally at least 99% homologous) to a naturally occurring protein.

In some embodiments, the protein (or protein fragment) is denatured.

It is to be understood that the protein described herein may optionally comprise more than one polypeptide chain.

In embodiments comprising a protein characterized by more than one polypeptide chain, the conjugate described herein optionally comprises one polypeptide of the protein.

Alternatively, the conjugate described herein comprises a plurality of polypeptides of the protein (e.g., all of the polypeptides of the protein). Optionally, the plurality of polypeptides are linked together (e.g., by non-covalent and/or covalent bonds) so as to form a multimer (e.g., a dimer, a trimer, a tetramer, a hexamer, etc.), the multimer having attached thereto at least two polymeric moieties, as described herein. Optionally, the polypeptides of the protein are separate (e.g., separated by denaturation of the protein), such that the conjugate described herein is a mixture of different conjugate species, wherein each of the conjugate species comprises a different polypeptide.

Optionally, the polypeptide (e.g., protein or protein fragment) is selected so as to exhibit a biological activity. Optionally, the biological activity comprises support for cell growth and/or invasion.

Examples of proteins exhibiting a biological activity which is advantageous in the context of embodiments of the present invention include, without limitation, a cell signaling protein, an extracellular matrix protein, a cell adhesion protein, a growth factor, protein A, a protease and a protease substrate. Optionally, the protein is an extracellular matrix protein.

According to optional embodiments, the polypeptide comprises a fibrinogen polypeptide (α, β and/or γ chains of fibrinogen) or a fragment thereof. Optionally, the conjugate described herein comprises the α, β and γ chains of fibrinogen. In exemplary embodiments, the polypeptide is a denatured fibrinogen (e.g., a mixture of denatured α, β and γ chains of fibrinogen).

Examples of extracellular matrix proteins include, but are not limited to, fibrinogen (e.g., α-chain—GenBank Accession No. NP_068657; β-chain—GenBank Accession No. P02675; γ-chain—GenBank Accession No. P02679), collagen (e.g., GenBank Accession No. NP_000079), fibronectin (e.g., GenBank Accession No. NP_002017), vimentin (e.g., GenBank Accession No. NP_003371), elastin, fibrillin, fibulin, laminin (e.g., GenBank Accession No. NP_000218) and gelatin.

Examples of cell signaling proteins include, but are not limited to, p38 mitogen-activated protein kinase (e.g., GenBank Accession No. NP_002736), nuclear factor kappaB (e.g., GenBank Accession No. NP_003989), Raf kinase inhibitor protein (RKIP) (e.g., GenBank Accession No. XP_497846), Raf-1 (e.g., GenBank Accession No. NP_002871), MEK (e.g., GenBank Accession No. NP_002746), protein kinase C(PKC) (e.g., GenBank Accession No. NP_002728), phosphoinositide-3-kinase gamma (e.g., GenBank Accession No. NP_002640), receptor tyrosine kinases such as insulin receptor (e.g., GenBank Accession No. NP_000199), heterotrimeric G-proteins (e.g., Galpha(i)-GenBank Accession No. NP_002060; Galpha(s)—GenBank Accession No. NP_000507; Galpha (q)—GenBank Accession No. NP_002063), caveolin-3 (e.g., GenBank Accession No. NP_001225), microtubule associated protein 1B, and 14-3-3 proteins (e.g., GenBank Accession No. NP_003397).

Examples of cell adhesion proteins include, but are not limited to, integrin (e.g., GenBank Accession No. NP_002202), intercellular adhesion molecule (ICAM) 1 (e.g., GenBank Accession No. NP_000192), N-CAM (e.g., GenBank Accession No. NP_000606), cadherin (e.g., GenBank Accession No. NP_004351), tenascin (e.g., GenBank Accession No. NP_061978), gicerin (e.g., GenBank Accession No. NP_006491), and nerve injury induced protein 2 (ninjurin2) (e.g., GenBank Accession No. NP_067606).

Examples of growth factors include, but are not limited to, epidermal growth factor (e.g., GenBank Accession No. NP_001954), transforming growth factor-β (e.g., GenBank Accession No. NP_000651), fibroblast growth factor-acidic (e.g., GenBank Accession No. NP_000791), fibroblast growth factor-basic (e.g., GenBank Accession No. NP_001997), erythropoietin (e.g., GenBank Accession No. NP_000790), thrombopoietin (e.g., GenBank Accession No. NP_000451), neurite outgrowth factor, hepatocyte growth factor (e.g., GenBank Accession No. NP_000592), insulin-like growth factor-I (e.g., GenBank Accession No. NP_000609), insulin-like growth factor-II (e.g., GenBank Accession No. NP_000603), interferon-γ (e.g., GenBank Accession No. NP_000610), and platelet-derived growth factor (e.g., GenBank Accession No. NP_079484).

Examples of proteases include, but are not limited to, pepsin (e.g., GenBank Accession No. NP_055039), low specificity chymotrypsin, high specificity chymotrypsin, trypsin (e.g., GenBank Accession No. NP_002760), carboxypeptidases (e.g., GenBank Accession No. NP_001859), aminopeptidases (e.g., GenBank Accession No. NP_001141), proline-endopeptidase (e.g. GenBank Accession No. NP_002717), *Staphylococcus aureus* V8 protease (e.g., GenBank Accession No. NP_374168), proteinase K (PK) (e.g., GenBank Accession No. P06873), aspartic protease (e.g., GenBank Accession No. NP_004842), serine proteases (e.g., GenBank Accession No. NP_624302), metalloproteases (e.g., GenBank Accession No. NP_787047), to ADAMTS17 (e.g., GenBank Accession No. NP_620688), tryptase-γ (e.g., GenBank Accession No. NP_036599), matriptase-2 (e.g., GenBank Accession No. NP_694564).

Examples of protease substrates include the peptide or peptide sequences being the target of the protease protein. For example, lysine and arginine are the target for trypsin; tyrosine, phenylalanine and tryptophan are the target for chymotrypsin.

Such naturally occurring proteins can be obtained from any known supplier of molecular biology reagents.

As exemplified in the Examples section below, it has been surprisingly uncovered that a conjugate comprising a polypeptide as described herein and at least one polymeric moiety exhibiting thermal gelation may provide the conjugate with an ability to undergo reverse thermal gelation.

Hence, according to optional embodiments, the conjugate is characterized by an ability to undergo reverse thermal gelation in an aqueous solution, as described herein.

Optionally, the reverse thermal gelation of the conjugate occurs at a temperature below 55° C., optionally below 50° C., optionally below 40° C., and optionally below 30° C. Optionally, the reverse thermal gelation occurs at a temperature below about 37° C., such that at a physiological temperature of about 37° C., the conjugate is in a gelled state.

Optionally, the reverse thermal gelation of the conjugate occurs at a temperature above 0° C., optionally above 10° C., optionally above 20° C. and optionally above 30° C.

In some embodiments, the reverse thermal gelation of the conjugate occurs upon an increase of temperature from 0° C. to 55° C., optionally from 10° C. to 55° C., optionally from 10° C. to 40° C., optionally from 15° C. to 37° C., and optionally from 20° C. to 37° C. Reverse thermal gelation which occurs upon an increase of temperature from a room temperature (e.g., about 20° C., about 25° C.) to a physiological temperature (e.g., about 37° C.) are particularly useful for some applications (e.g., medical applications), as gelation can be induced by transfering the conjugate from a room temperature environment to a physiological temperature, for example, by placing the conjugate in a body.

As exemplified herein, the temperature at which gelation of a conjugate solution occurs may be controlled by varying the concentration of the conjugate.

Furthermore, the gelation temperature may be controlled by selecting a polymer with an appropriate gelation temperature for inclusion in the polymeric moiety, and/or by varying the concentration of polymeric moieties which exhibit reverse thermal gelation (e.g., by varying the number of polymeric moieties attached to a polypeptide and/or by varying the size of the polymeric moieties).

As further exemplified in the Examples section, aqueous solutions comprising conjugates described herein may undergo reverse thermal gelation at relatively low concentrations, for example, less than 20 weight percents conjugate, optionally less than 10 weight percents, optionally less than 5 weight percents, and optionally less than 2 weight percents.

Without being bound by any particular theory, it is believed that conjugation of a polypeptide to a polymer exhibiting reverse thermal gelation acts as chain extension of the polymer, which lowers the minimal concentration necessary for gelation.

It is to be noted that a phenomenon of a chain extender of a biological nature or origin (e.g., a polypeptide) has never been reported heretofore.

The reverse thermal gelation of the conjugate as described herein can be determined by measuring a shear storage modulus of an aqueous solution containing same. An temperature-dependent increase in the storage modulus is indicative of a gel formation via a reverse thermal gelation.

As used herein and in the art, a "shear modulus" is defined as the ratio of shear stress to the shear strain. The shear modulus may be a complex variable, in which case the "storage modulus" is the real component and the "loss modulus" is the imaginary component. The storage modulus and loss modulus in viscoelastic solids measure the stored energy, representing the elastic portion, and the energy dissipated as heat, representing the viscous portion.

In some embodiments, the reverse thermal gelation described herein increases a shear storage modulus (also referred to herein as "storage modulus", or as "G'") of the aqueous solution of the conjugate by at least ten-folds, optionally at least 30-folds, optionally at least 100-folds, and optionally at least 300-folds.

In some embodiments, the reverse thermal gelation described herein increases a shear storage modulus of the aqueous solution to at least 5 Pa, optionally at least 15 Pa, optionally at least 20 Pa, optionally at least 50 Pa, optionally at least 100 Pa, and optionally at least 200 Pa.

In some embodiments, the shear storage modulus of the aqueous solution containing the conjugate before reverse thermal gelation (e.g., at a temperature below a temperature at which gelation occurs) is less than 2 Pa, optionally less than 1 Pa, optionally less than 0.5 Pa, and optionally less than 0.2 Pa.

According to optional embodiments, the reverse thermal gelation is reversible, i.e., a gelled state obtained by increasing a temperature can revert to the non-gelled state by lowering the temperature, the non-gelled state having substantially the same properties as existed prior to the reverse thermal gelation. Reversible gelation is advantageous in that a gelled state can be modified and/or reconstructed by causing at least a portion of the gelled state to revert to a non-gelled state (by decreasing a temperature), followed by formation of a gelled state (by increasing a temperature) in a desired form. In addition, reversible gelation does not create spoilage of a product by gelation before a product is used (e.g., a product in storage), as any such gelation prior to use of the product may be eliminated (by cooling).

Optionally, the gelation is reversible over many cycles (e.g., at least 10 cycles, at least 50 cycles) of increasing and decreasing a temperature.

Optionally, a gel formed by reverse thermal gelation of an aqueous solution of the conjugate is a biodegradable gel, i.e., the gel degrades in contact with a tissue and/or a cell (e.g., by proteolysis and/or hydrolysis). Biodegradable materials are useful in various medical applications, for example as temporary implants. In addition, biodegradable materials are highly suitable as matrices for supporting cell growth and/or migration, as cell growth and/or migration is associated with degradation of a surrounding matrix.

As exemplified in the Examples section below, a gel formed by reverse thermal gelation of a solution of a conjugate described herein may serve as a suitable matrix for cell growth, spreading, expansion and/or invasion.

Hence, the conjugate described herein is optionally identified for use in generating a scaffold, as defined herein. The scaffold may be generated by reverse thermal gelation of the conjugate (e.g., by non-covalent cross-linking of the conjugate) and/or by covalent cross-linking of the conjugate.

The conjugate described herein can therefore be referred to also as a precursor molecule for generating a scaffold. Thus, the scaffold is formed by cross-linking (covalently and/or non-covalently) a plurality of precursor molecules to one another.

As used herein, the term "scaffold" describes a two-dimensional or a three-dimensional supporting framework. The scaffold according to embodiments of the present invention is composed of precursor units (comprising the conjugates as described herein) which are cross-linked therebetween. In some embodiments, a scaffold can be used as a support for cell growth, attachment and/or spreading and thus facilitates tissue generation and/or tissue repair. In some embodiments, a scaffold maintains a desired shape of a tissue and/or cell colony supported thereby.

In exemplary embodiments, the scaffold is a hydrogel, i.e., the gel formed from the conjugate comprises water absorbed therein, for example, water from an aqueous solution of the conjugate which underwent gelation.

As used herein and is well-known in the art, the term "hydrogel" refers to a material that comprises solid networks formed of water-soluble natural or synthetic polymer chains, typically containing more than 99% water.

Optionally the hydrogel is characterized by a shear storage modulus of at least 15 Pa (optionally at least 50 Pa, optionally at least 100 Pa, and optionally at least 200 Pa) at 37° C.

Optionally the generation of the scaffold is reversible. Reversible scaffold generation is optionally obtained in embodiments wherein scaffold generation is by reverse thermal gelation, as discussed hereinabove.

Optionally, the scaffold is generated by means other than reverse thermal gelation, for example, by covalent cross-linking. The obtained scaffold (e.g., a hydrogel) is optionally capable of further undergoing a reverse thermal gelation. Further optionally, the scaffold is generated by a reverse thermal gelation and is thereafter further subjected to covalent cross-linking, as described herein.

As discussed herein, conjugates described herein may be cross-linked by non-covalent (physical) cross-linking and/or by covalent (chemical) cross-linking.

Hence, according to another aspect of embodiments of the invention, there is provided a composition-of-matter (e.g., a scaffold or a hydrogel) comprising a cross-linked form of a conjugate described herein. The composition-of-matter thus comprises a plurality of molecules of the conjugate cross-linked to one another.

It is to be understood that although the composition-of-matter is described herein to for the sake of simplicity as comprising a conjugate, compositions-of-matter comprising a plurality of conjugate species (e.g., a mixture of different conjugates) are encompassed by the term "composition-of-matter".

In some embodiments, the conjugate molecules are cross-linked non-covalently.

Optionally the molecules are cross-linked only non-covalently (i.e., no substantial covalent cross-linking is present).

Compositions-of-matter described herein may optionally be generated by non-covalent and/or covalent cross-linking of the conjugate molecules in a solution, preferably an aqueous solution. Optionally, the solution remains absorbed to the cross-linked conjugate, for example, in the form of a gel (e.g., a hydrogel).

The solution may be selected suitable for effecting the abovementioned covalent and/or non-covalent cross-linking.

In some embodiments, the solution is an aqueous solution.

Compositions-of-matter comprising only non-covalent cross-linking may optionally be generated by reverse thermal gelation of the conjugate molecules in an aqueous solution (e.g., as described herein). Optionally, the non-covalently cross-linked form is reversible, as described herein.

In some embodiments, the conjugate molecules are cross-linked covalently. In such embodiments, the conjugate comprises a cross-linking moiety (as described herein). The composition-of-matter is optionally generated by subjecting a plurality of conjugate molecules to conditions for effecting covalent cross-linking of the cross-linking moieties of the conjugate molecules.

Optionally the covalently cross-linked composition-of-matter is characterized by a shear storage modulus of at least 20 Pa at 37° C., and optionally at least 50 Pa, optionally at least 100 Pa, optionally at least 200 Pa, and optionally at least 300 Pa.

In some embodiments a composition-of-matter comprises non-covalent cross-linking, in addition to the covalent cross-linking.

For example, a composition-of-matter comprising covalent cross-linking may be capable of undergoing reverse thermal gelation (e.g., a reversible reverse thermal gelation).

Such a reverse thermal gelation of a covalently cross-linked composition-of-matter may optionally increase a shear storage modulus of the composition-of-matter by at least 20%, optionally at least 50%, optionally at least 200%, optionally at least 400%, and optionally at least 900%.

The shear storage modulus prior to reverse thermal gelation is optionally in a range of from 0.5 Pa to 200 Pa, optionally in a range of from 0.5 Pa to 100 Pa, and optionally in a range of from 10 Pa to 100 Pa.

The shear storage modulus following reverse thermal gelation is optionally at least 15 Pa, and optionally in a range of from 20 Pa to 5000 Pa, optionally from 20 Pa to 1000 Pa, optionally from 20 Pa to 500 Pa, and optionally from 50 Pa to 500 Pa.

Optionally, the reverse thermal gelation of a covalently cross-linked composition-of-matter is at a temperature described herein for gelation of a conjugate.

As exemplified in the Examples section below, a composition-of-matter may be characterized by a shear storage modulus of one portion of the composition-of-matter that is different from a shear storage modulus of at least one other portion of the composition-of-matter. Each portion may independently be characterized by non-covalent cross-linking, covalent cross-linking or a combination of non-covalent and covalent cross-linking (e.g., as described hereinabove).

Such a composition-of-matter may be prepared, for example, using two solutions of a conjugate (e.g., solutions of different conjugates and/or solutions with different concentrations of conjugate). Optionally, one solution is cross-linked to obtain a first composition-of-matter (e.g., as described herein), whereupon the first composition-of-matter is added to the second solution. Upon cross-linking of the second solution (e.g., under conditions which do not significantly affect the first composition-of-matter), a composition-of-matter having portions with different properties may be obtained.

Regardless of the type (non-covalent and/or covalent) of cross-linking, compositions-of-matter described herein are optionally biodegradable. In some embodiments, the incorporation of a polypeptide in a network of cross-linked conjugates within the composition-of-matter causes the composition-of-matter to biodegrade upon biodegradation of the polypeptide.

According to optional embodiments, the composition-of-matter further comprises cells (preferably live cells) therein. The cells may comprise one cell type or a to two or more cell types.

Compositions-of-matter described herein may be useful for inducing formation of a tissue, for example, by serving as a matrix for supporting cellular growth and/or invasion, and/or by providing cells (e.g., embedded in the composition-of-matter) which induce tissue formation. Such properties may be useful for repairing tissue damage.

Hence, in some embodiments, the composition-of-matter is identified for use in inducing formation of a tissue, as discussed in further detail hereinbelow.

In some embodiments, the composition-of-matter is identified for use in repairing tissue damage, as discussed in further detail hereinbelow.

The compositions-of-matter described herein may be prepared by various processes, depending on the type of composition-of-matter, and particularly, on the type of cross-linking (i.e., non-covalent and/or covalent) in the composition-of-matter.

Thus, according to another aspect of embodiments of the invention, there is provided a process of producing a composition-of-matter which comprises non-covalent cross-linking (e.g., as described herein). The process comprises heating a solution (e.g., an aqueous solution) which comprises a plurality of molecules of a conjugate as described herein, from a first temperature to a second temperature. The second temperature is such that a reverse thermal gelation of the conjugate in solution is effected, thereby producing a composition-of-matter with non-covalent cross-linking.

The second temperature is a temperature at or above the critical temperature of the precursor conjugate, as detailed hereinabove.

Optionally, the composition-of-matter is produced in vivo, for example, by heating to a physiological temperature (e.g., about 37° C.). Such heating may be effected simply by contacting a solution of the conjugate with a body.

In some embodiments, the conjugate is a conjugate comprising at least one cross-linking moiety described herein, and the process further comprises subjecting the conjugate solution to conditions that effect cross-linking of the cross-linking moieties (e.g., prior to the aforementioned heating, subsequent to the heating or concomitant with the heating). Cross-linking of the cross-linking moieties may optionally be performed so as to obtain a composition-of-matter comprising both non-covalent and covalent cross-linking.

According to another aspect of embodiments of the invention, there is provided a process of producing a composition-of-matter which comprises covalent cross-linking (e.g., as described herein). The process comprises subjecting a solution comprising a plurality of molecules of a conjugate described herein, wherein the conjugate comprises at least one cross-linking moiety (as described herein), to conditions that effect covalent cross-linking of the cross-linking moieties, thereby producing a composition-of-matter with covalent cross-linking.

Optionally, the covalent cross-linking is effected in vivo.

Alternatively, the covalent cross-linking is effected ex vivo.

Optionally, the process further comprises forming non-covalent cross-links, for example, by exposure to a temperature at which reverse thermal gelation occurs.

In some embodiments, covalent cross-linking is effected ex vivo, to thereby produce a covalently cross-linked scaffold, and the process further comprises subjecting the covalently cross-linked scaffold to a physiological temperature in vivo (e.g., by contacting the scaffold with a body), such that reverse thermal gelation of the scaffold is effected in vivo, thereby producing a composition-of-matter in vivo which comprises non-covalent and covalent cross-linking.

In some embodiments, the solution of the conjugate further comprises cells. Consequently, the process produces a composition-of-matter comprising cells embedded therein (as described herein).

The conditions which effect cross-linking of cross-linking moieties will depend on the chemical properties of the cross-linking moieties.

Various conditions for effecting cross-linking are known in the art. For example, cross-linking may be effected by irradiation (e.g., by UV light, by visible light, by ionizing radiation), by an initiator (e.g., free radical donors) and/or heat.

Preferably, the conditions for effecting covalent cross-linking are biocompatible, namely, use agents or conditions which are not considered as hazardous in in vivo applications.

According to an optional embodiment of the present invention, the cross-linking is by illumination with UV (e.g., at a wavelength of about 365 nm).

As used herein the term "about" refers to ±10%.

When cross-linking in vivo, it is preferable to avoid irradiation doses that are harmful. The maximal dose which is non-harmful will depend, for example, on the type (e.g., wavelength) of irradiation, and on the part of the body exposed to the irradiation. One skilled in the art will readily be capable of determining whether a dose is harmful or non-harmful.

In some embodiment, the conditions comprise a presence of an initiator which is added to facilitate cross-linking.

Optionally, the initiator is capable of effecting cross-linking without irradiation.

Alternatively, the initiator is a photoinitiator which effects cross-linking in the presence of irradiation (e.g., UV light, visible light). Addition of a photoinitiator will typically enable one to use lower doses of UV light for cross-linking.

As used herein, the term "photoinitiator" describes a compound which initiates a chemical reaction (e.g., cross-linking reaction, chain polymerization) when exposed to UV or visible illumination. Many suitable photoinitiators will be known to one skilled in the art. Exemplary photoinitiators include, without limitation, bis(2,4,6-trimethylbenzoyl) phenylphosphine oxide (BAPO), 2,2-dimethoxy-2-phenylacetophenone (DMPA), camphorquinone (CQ), 1-phenyl-1,2-propanedione (PPD), the organometallic complex Cp'Pt(CH(3))(3) (Cp'=eta(5)-C(5)H(4)CH(3)), 2-hydroxy-1-[4-(hydroxyethoxy)phenyl]-2-methyl-1-propanone (e.g., Irgacure™ 2959), dimethylaminoethyl methacrylate (DMAEMA), 2,2-dimethoxy-2-phenylacetophenone, benzophenone (BP), and flavins.

As exemplified in the Examples section below, physical properties (e.g., shear storage modulus) of compositions-of-matter depend on certain parameters which may be readily controlled. Thus, a composition-of-matter having a desired physical property may be prepared by selecting a suitable value of one or more of such parameters.

Hence, according to another aspect of embodiments of the invention, there is provided a method of controlling a physical property (e.g., a shear storage modulus) of a composition-of-matter such as described herein. The method comprises controlling a parameter which characterizes the composition-of-matter. Such a parameter can be, for example, a concentration of a conjugate described herein in the solution (aqueous solution), an ambient temperature, a cross-linking temperature. In addition, the parameter can be the presence or absence of covalent cross-linking, a concentration of initiator (e.g., a presence or absence of initiator) during covalent cross-linking, and/or a dose of irradiation used for covalent cross-linking.

The concentration of a conjugate in a composition-of-matter may be readily controlled by preparing a solution of the conjugate at a selected concentration, and cross-linking the conjugate by covalent and/or non-covalent cross-linking, as described herein, such that the solution of the conjugate is converted into a composition-of-matter described herein, having the selected concentration of conjugate.

In some embodiments, the concentration of conjugate is positively correlated with the shear storage modulus, as exemplified in the Examples herein.

In some embodiments, the concentration of conjugate is negatively correlated with a temperature at which reverse thermal gelation is effected (e.g., a critical gelation temperature), as exemplified in the Examples herein.

In some embodiments, the ambient temperature controls a physical property of a composition-of-matter by affecting reverse thermal gelation of a composition-of-matter, as described herein.

The ambient temperature may be selected, for example, such that gelation is not effected (e.g., at a relatively low temperature) and the shear storage modulus is relatively low, such that gelation is effected (e.g., at a relatively high temperature) and the shear storage modulus is relatively high. In addition, an ambient temperature may be selected (e.g., at an intermediate temperature) such that gelation is partially effected to any desired degree, such that the shear storage can be at any intermediate level which is desired.

Typically, the composition-of-matter will be characterized by a relatively narrow temperature range (e.g., a 5° C. range, a 10° C. range, a 15° C. range) in which a physical property (e.g., a shear storage modulus) exhibits a particularly strong temperature dependence. Optionally, an ambient temperature is selected from within this temperature range, such that the physical property may be conveniently controlled by relatively small changes in ambient temperature.

The cross-linking temperature (i.e., a temperature at which conjugates in the composition-of-matter are covalently cross-linked) may be used to control a physical property of a composition-of-matter which comprises covalent cross-linking (e.g., as described herein).

In some embodiments, the cross-linking temperature is negatively correlated with a shear storage modulus of the composition-of-matter, as exemplified in the Examples herein.

In some embodiments, a correlation between a physical property (e.g., shear storage modulus) and cross-linking temperature is particularly strong when the cross-linking temperature is in a temperature range in which a physical property exhibits a particularly strong temperature-dependence, as described hereinabove. Optionally a cross-linking temperature is selected from within this temperature range, such that the physical property may be conveniently controlled by relatively small changes in cross-linking temperature.

In some embodiments, the presence of covalent cross-linking is associated with a higher shear storage modulus, as exemplified herein.

In some embodiments, a degree of covalent cross-linking by modulating the conditions for effecting covalent cross-linking.

Thus, for example, low degree of covalent cross-linking may be obtained by effecting covalent cross-linking without an initiator or with a smaller amount of initiator, and/or without irradiation or with a small dose of irradiation (e.g., using a short irradiation time and/or a low intensity of irradiation).

In some embodiments, the parameter (e.g., ambient temperature, cross-linking temperature) is relatively independent of some physical properties (e.g., biodegradation rate). This advantageously allows for controlling two or more physical properties of interest (e.g., degradation rate and shear storage modulus) without creating a need for experimentation to determine how such physical properties are interdependent. For example, a shear storage modulus may optionally be controlled by selecting a suitable cross-linking temperature, while a degradation rate may be controlled by selecting an appropriate polymer for the polymeric moieties described herein.

Thus, in some embodiments, changing a parameter described herein (e.g., ambient temperature, cross-linking temperature) will change a biodegradation rate by a factor of less than 4, optionally by a factor of less than 3, optionally by a factor of less than 2, and optionally by a factor of less than 1.5.

The biodegradation rate is optionally quantified by measuring a half-life of the composition-of-matter in a trypsin solution (e.g., using procedures described herein).

Conjugates according to embodiments of the invention may be produced in a relatively simple and inexpensive manner.

Thus, according to another aspect of embodiments of the invention, there is provided a process of producing a conjugate as described herein, the process comprising covalently attaching a polymer to a polypeptide, the polymer and polypeptide being such that at least two polymer molecules attach to a molecule of the polypeptide, wherein at least one of the two polymer molecules exhibits a reverse thermal gelation.

The polymer may optionally comprise at least one cross-linking moiety (e.g., as described herein), so as to produce a conjugate comprising at least one cross-linking moiety, as described herein.

Optionally, the polymer comprises at least one first moiety (optionally a single first moiety) which is capable of reacting so as to attach the polymer to the polypeptide, and optionally at least one second moiety which is a cross-linking moiety described herein.

In some embodiments, the first moiety and the second moiety are different, such that the first moiety may be reacted so as to attach the polymer to the polypeptide, without causing the second moiety (cross-linking moiety) to react prematurely (e.g., before cross-linking of conjugate molecules is desired).

In some embodiments, the first moiety and second moiety are the same, the moiety being suitable for attaching the polymer to the polypeptide and for cross-linking the conjugate.

Optionally, such a cross-linking moiety is selected as being capable of undergoing two different reactions, each under different conditions, such that the moiety may be reacted under one set of conditions so as to attach the polymer to the polypeptide, and then reacted under different conditions so as to cross-link conjugate molecules. For example, as described herein, some unsaturated moieties (e.g., acrylates) may undergo Michael-type addition by a thiol (e.g., under basic conditions) so as to attach the polymer to a polypeptide, and also undergo polymerization (e.g., under conditions for initiating free radical polymerization) so as to cross-link conjugaes.

In some embodiments wherein the first and second moieties described herein are the same (or otherwise capable of undergoing similar reactions under the same conditions), the polypeptide is reacted with a molar excess (e.g., at least 20:1, at least 50:1, at least 100:1, at least 200:1) of the polymer, so as to prevent each polymer molecule from attaching to more than one site on the polypeptide.

Apart from being inexpensive to produce, the compositions-of-matter of embodiments of the present invention are highly reproducible, flexible (can be stressed or stretched easily), exhibit controllable structural properties, and are amenable to controllable biodegradation; characteristics which make it highly suitable for in vivo or ex vivo regeneration of tissues such as bone, cartilage, heart muscle, skin tissue, blood vessels, and other tissues (soft and hard) in the body. For example, such a scaffold hydrogel can be easily placed into gaps within a tissue or an organ, following which it can fill the void and initiate the process of regeneration as the scaffold degrades away.

Hence, according to another aspect of embodiments of the invention, there is provided a use of a conjugate described herein or of a composition-of-matter described herein in the manufacture of a medicament for repairing tissue damage.

The medicament is optionally for inducing formation of a tissue (in vivo and/or ex vivo).

Optionally, the medicament is for treating a disorder characterized by tissue damage or loss (e.g., as described herein). Herein, the phrase "tissue" refers to part of an organism consisting of an aggregate of cells having a similar structure and function. Examples include, but are not limited to, brain tissue, retina, skin tissue, hepatic tissue, pancreatic tissue, bone, cartilage, connective tissue, blood tissue, muscle tissue, cardiac tissue brain tissue, vascular tissue, renal tissue, pulmunary tissue, gonadal tissue, hematopoietic tissue and fat tissue. Preferably, the phrase "tissue" as used herein also encompasses the phrase "organ" which refers to a fully differentiated structural and functional unit in an animal that is specialized for some particular function. Non-limiting examples of organs include head, brain, eye, leg, hand, heart, liver kidney, lung, pancreas, ovary, testis, and stomach.

According to another aspect of embodiments of the invention, there is provided a use of a conjugate described herein or of a composition-of-matter described herein in the manufacture of a medicament for treating a subject having a disorder characterized by tissue damage or loss.

As used herein the phrase "disorder characterized by tissue damage or loss" refers to any disorder, disease or condition exhibiting a tissue damage (e.g., non-functioning tissue, cancerous or pre-cancerous tissue, broken tissue, fractured tissue, fibrotic tissue, or ischemic tissue) or a tissue loss (e.g., following a trauma, an infectious disease, a genetic disease, and the like) which require tissue regeneration. Examples for disorders or conditions requiring tissue regeneration include, but are not limited to, liver cirrhosis such as in hepatitis C patients (liver tissue), type-1 diabetes (pancreatic tissue), cystic fibrosis (lung, liver, pancreatic tissue), bone cancer (bone tissue), burn and wound repair (skin tissue), age related macular degeneration (retinal tissue), myocardial infarction, myocardial repair, CNS lesions (myelin), articular cartilage defects (chondrocytes), bladder degeneration, intestinal degeneration, and the like. In addition, cosmetic tissue damage or loss is encompassed by the term "disorder".

As used herein, the term "cosmetic" refers to apparent (e.g., visible) tissue, including, but not limited to, skin tissue. Cosmetic tissue damage or loss is typically detrimental aesthetically, and may be detrimental for additional reasons (e.g. psychological factors).

Herein, the phrase "treating" refers to inhibiting or arresting the development of a disease, disorder or condition and/or causing the reduction, remission, or regression of a disease, disorder or condition in an individual suffering from, or diagnosed with, the disease, disorder or condition. Those of skill in the art will be aware of various methodologies and assays which can be used to assess the development of a disease, disorder or condition, and similarly, various methodologies and assays which can be used to assess the reduction, remission or regression of a disease, disorder or condition.

In some embodiments, a medicament comprising a conjugate as described herein is identified for being cross-linking the conjugate (in vivo and/or ex vivo), as described herein.

In some embodiments, a medicament comprising a composition-of-matter described herein is identified for being implanted in a subject.

As used herein, the term "subject" refers to a vertebrate, preferably a mammal, more preferably a human being (male or female) at any age.

Implantation is optionally effected using a surgical tool such as a scalpel, spoon, spatula, or other surgical devices. Optionally, implantation is effected via injection (e.g. via syringe, catheter, and the like)

Herein, the terms "implant" and "implantation" encompass placing a substance (e.g., a conjugate or composition-of-matter described herein) in a body or on a body surface (e.g., on a skin surface). According to another aspect of embodiments of the invention, there is provided a method of inducing formation of a tissue in vivo, the method comprising implanting a composition-of-matter described herein in a subject (e.g., as described herein), to thereby induce the formation of the tissue.

In some embodiments, the composition-of-matter is a composition-of-matter which comprises covalently cross-linked conjugate as described herein, and is non-covalently cross-linked in vivo following implantation (e.g., to provide the composition-of-matter with a desired rigidity). Optionally, the non-covalent cross-linking is effected by exposure to a physiological temperature (e.g., as described herein), the exposure to the physiological temperature being a direct result of implantation.

According to another aspect of embodiments of the invention, there is provided a method of inducing formation of a tissue in vivo, the method comprising implanting a plurality of molecules of a conjugate described herein in a subject, to thereby induce the formation of the tissue.

In some embodiments, the conjugate is non-covalently cross-linked in vivo following implantation (e.g., to form a scaffold). Optionally, the non-covalent cross-linking is effected by exposure to a physiological temperature (e.g., as described herein), the exposure to the physiological temperature being a direct result of implantation.

In some embodiments, the conjugate is covalently cross-linked in vivo following implantation (e.g., to form a scaffold). Cross-linking can be performed as described herein, using non-toxic, non-hazardous agents and/or conditions (e.g., application of UV irradiation).

According to another aspect of embodiments of the invention, there is provided a method of inducing formation of a tissue ex vivo, the method comprising subjecting a composition-of-matter having cells therein (as described herein) to conditions conductive to growth of the cells, to thereby induce tissue formation.

As used herein, the phrase "ex vivo" refers to living cells which are derived from an organism and are growing (or cultured) outside of the living organism, for example, outside the body of a vertebrate, a mammal, or human being. For example, cells which are derived from a human being such as human muscle cells or human aortic endothelial cells and cultured outside of the body are referred to as cells which are cultured ex vivo.

The cells in a composition-of-matter described herein are optionally selected so as to be capable of forming a tissue. Such cells can be, for example, stem cells such as embryonic stem cells, bone marrow stem cells, cord blood cells, mesenchymal stem cells, adult tissue stem cells, or differentiated cells such as neural cells, retinal cells, epidermal cells, hepatocytes, pancreatic cells, osseous cells, cartilaginous cells, elastic cells, fibrous cells, myocytes, myocardial cells, endothelial cells, smooth muscle cells, and hematopoietic cells.

The composition-of-matter comprising cells may comprise cells embedded within and/or on the surface of the composition-of-matter. Cells may optionally be embedded within the composition-of-matter by cross-linking a conjugate described herein in the presence of cells (e.g., as described herein). Incorporation of cells onto a surface of the composition-of-matter may optionally be effected by contacting a prepared composition-of-matter with the cells.

The concentration of cells in and/or on the composition-of-matter depends on the cell type and the scaffold properties. Those of skill in the art are capable of determining the concentration of cells used in each case.

The composition-of-matter is optionally contacted with tissue culture medium and growth factors.

Alternatively or additionally, the composition-of-matter comprises tissue culture medium and growth factors, for example, in an aqueous phase of a hydrogel.

Optionally, the cells are routinely examined (e.g., using an inverted microscope) for evaluation of cell growth, spreading and tissue formation, in order to facilitate control over the tissue formation, and/or to determine when a process of tissue formation has been completed.

Following ex vivo tissue formation, the obtained tissue and/or composition-of-matter comprising the formed tissue is optionally implanted in the subject (e.g., to induce further tissue formation, to repair tissue damage, and/or to treat a disorder as described herein). Those of skills in the art are capable of determining when and how to implant the tissue and/or composition-of matter to thereby induce tissue formation and/or repair, and/or to treat a disease described herein.

It will be appreciated that the cells to be implanted in a subject (e.g., for inducing in vivo tissue formation and/or following ex vivo formation of a tissue), as described herein, may optionally be derived from the treated subject (autologous source), and optionally from allogeneic sources such as embryonic stem cells which are not expected to induce an immunogenic reaction.

According to another aspect of embodiments of the invention, there is provided a method of treating a subject having a disorder characterized by tissue damage or loss (e.g., as described herein), the method comprising implanting a composition-of-matter described herein in a subject, as described herein, to thereby induce formation of the tissue, thereby treating the disorder characterized by tissue damage or loss.

According to another aspect of embodiments of the invention, there is provided a method of treating a subject having a disorder characterized by tissue damage or loss (e.g., as described herein), the method comprising implanting a plurality of molecules of a conjugate described herein in a subject, as described herein, to thereby induce formation of the tissue, thereby treating the disorder characterized by tissue damage or loss.

In some embodiments of the methods described herein which are effected by implanting a conjugate, the conjugate optionally comprises at least one cross-linking moiety (e.g., as described herein). In such embodiments, the method optionally further comprising covalently cross-linking the plurality of molecules of the conjugate, for example, by subjecting the plurality of molecules to conditions (e.g., as described herein) that effect covalent cross-linking of the cross-linking moieties of the molecules.

A conjugate described herein may be provided as a composition, for example a composition for effecting a method or use described herein. The composition may be for effecting a pharmaceutical (e.g., medicinal) treatment and/or a cosmetic treatment (e.g., as described herein).

Hence, according to another aspect of embodiments of the invention, there is provided a pharmaceutical, cosmetic or cosmeceutical composition comprising a plurality of molecules of a conjugate described herein, the composition being identified for use in inducing formation of a tissue upon being contacted with a tissue and further upon subjecting the composition to a physiological temperature.

Herein, the phrase "cosmeceutical composition" refers to a composition characterized by both pharmaceutical and cosmetic uses.

Optionally, the conjugate comprises at least one cross-linking moiety (as described herein), and the composition is identified for use in inducing formation of a tissue upon further subjecting the plurality of molecules of the conjugate to conditions (e.g., as described herein) that effect covalent cross-linking of the cross-linking moieties of the molecules.

Optionally, the composition further comprises an initiator (e.g., as described herein) for inducing the covalent cross-linking of the cross-linking moieties.

Optionally, the composition described herein is packaged in a packaging material and identified in print, in or on the packaging material, for use in inducing formation of tissue and/or for treating a disorder, as described herein.

The composition may further comprise a pharmaceutically acceptable carrier, and be formulated for facilitating its administration (e.g., implantation).

Herein, the term "pharmaceutically acceptable carrier" refers to a carrier or a diluent that does not cause significant irritation to an organism and does not abrogate the biological activity and properties of the administered compound. Examples, without limitations, of carriers are: propylene glycol, saline, emulsions and mixtures of organic solvents with water, as well as solid (e.g., powdered) and gaseous carriers.

Optionally, the carrier is an aqueous carrier, for example, an aqueous solution (e.g., saline).

The conjugate may also be provided as part of a kit.

Thus, according to another aspect of embodiments of the invention, there is provided a kit for inducing formation of a tissue, the kit comprising a conjugate described herein, an aqueous solvent, and instructions for cross-linking an aqueous solution of the conjugate in order to form a scaffold for inducing formation of tissue.

Optionally, the conjugate and solvent are stored separately within the kit (e.g., in separate packaging units), such that the conjugate is stored in a dry state until being contacted with the solvent for formation of a solution of the conjugate (e.g., a solution described herein). Such storage of the conjugate prior to use may increase an effective life span of the conjugate (and kit).

Optionally, the conjugate comprises at least one cross-linking moiety (e.g., as described herein), and the kit further comprises an initiator (e.g. as described herein) for inducing covalent cross-linking of the cross-linking moiety.

Optionally, the kit further comprises cells for embedding in the scaffold (e.g., as described herein).

The cells may form a part of the solvent or may be packaged separately.

In some embodiments, the kit comprises instructions as a package insert.

Instructions for cross-linking the conjugate in the solvent can be, for example, mixing the conjugate and solvent and subjecting the obtained solution to a certain temperature (e.g., for effecting reverse thermal gelation).

For example, if gelation of the conjugate is effected at ambient temperature, instructions may be to store the kit under refrigeration (e.g., below 10° C. or at 4° C.), mix the components at room temperature and wait until gel formation is observed.

If gelation is effected at higher temperatures, instructions may be to mix the components and then heat the solution for an indicated time period.

If covalent cross-linking is to be effected by irradiation, instructions may be to mix the components (optionally including a photoinitiator as described herein), irradiate the solution, and optionally heating the solution to effected thermal gelation as described hereinabove. The irradiation can be prior to, concomitant with or after irradiation.

If covalent cross-linking is to be effected by free radical polymerization, instructions may be to mix the components (including a polymerization initiator as described herein), and optionally heating the solution to effect thermal gelation as described hereinabove and/or to effect polymerization (if heating is desired). The heating to effect thermal gelation and to effect polymerization can be to the same temperature or to different temperatures.

In some embodiments, the conjugate and the solution are packaged within the kit at a ratio suitable for obtaining a composition-of-matter with the desired properties. Such a ratio can be pre-determined as detailed hereinabove.

Optionally, the instructions further include guidance for selecting a suitable ratio for obtaining a suitable property of the composition-of-matter, in accordance with the description provided hereinabove.

The instructions may further include guidance with regard to selecting the cross-linking conditions (e.g., with or without irradiation; with or without heating; with or without adding a polymerization initiator) for obtaining a composition-fof-matter with desired properties.

It is expected that during the life of a patent maturing from this application many relevant polymers exhibiting reverse thermal gelation will be developed and the scope of the phrase "polymeric moieties exhibiting a reverse thermal gelation" is intended to include all such new technologies a priori.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Materials and Methods

Materials:
Acetone was obtained from Bio-Lab (Israel);
acryloyl-chloride was obtained from Merck;
calcein AM was obtained from Sigma-Aldrich;
collagen type-I was obtained from BD Biosciences;
collagenase 1A was obtained from Sigma-Aldrich;
dichloromethane was obtained from Aldrich;
diethyl ether was obtained from Frutarom (Israel);
Dulbecco's modified Eagle medium was obtained from Gibco;
ethidium homodimer-1 was obtained from Sigma-Aldrich;
fetal bovine serum was obtained from Biological Industries (Israel);
formalin was obtained from Sigma-Aldrich;
Hoechst 33342 was obtained from Sigma Aldrich;
Irgacure® 2959 initiator was obtained from Ciba;
mercaptoethanol was obtained from Gibco;
N-hydroxysuccinimide-fluorescein was obtained from Thermo Scientific;
non-essential amino acids wee obtained from Biological industries (Israel);
penicillin-streptomycin was obtained from Biological Industries (Israel);
petroleum ether 40-60 was obtained from Bio-Lab (Israel);
Pluronic® F127 (12.6 kDa) was obtained from Sigma;
poly(ethylene glycol) (12 kDa) was obtained from Fluka;
sodium azide was obtained from Riedel-deHaen;
Tetronic® tetraol T1307 was obtained from BASF;
toluene was obtained from Bio-Lab (Israel);
triethylamine was obtained from Fluka;
tris(2-carboxyethyl)phosphine hydrochloride was obtained from Sigma;
trypsin was obtained from MP Biomedicals.

F127 Poloxamer-Diacrylate, Tetronic® T1307-Tetraacrylate and PEG-Diacrylate Synthesis:

F127 poloxamer-diacrylate (F127-DA), Tetronic® T1307-tetraacrylate (T1307-TA) and poly(ethylene glycol)-diacrylate (PEG-DA) were prepared from Pluronic® F127 (12.6 kDa), Tetronic® tetraol T1307 (18 kDa) and poly(ethylene glycol) (PEG) diol (12 kDa), respectively, according to the procedures described in Halstenberg et al. [*Biomacromolecules* 2002, 3:710-723]. As depicted in FIG. 1A, acrylation of the polymers was carried out under argon by reacting the hydroxyl-terminated polymers in a solution of dichloromethane and toluene with acryloyl chloride (Merck, Darmstadt, Germany) and triethylamine at a molar ratio of 1.5:1 relative to the hydroxyl groups. The final product was precipitated in ice-cold diethyl ether (for PEG-DA) or petroleum ether 40-60 (for F127-DA and T1307-TA). The solid polymer was dried under vacuum for 48 hours.

Using proton NMR, the average number of acryl groups per F127-DA molecule was determined to be 2.15, the average number of acryl groups per T1307-TA molecule was determined to be 4.38, and the average number of acryl groups per PEG-DA was determined to be 1.74.

Rheological Characterization:

Rheological measurements were carried out using an AR-G2 rheometer (TA Instruments) equipped with a Peltier plate temperature-controlled base. A 40 mm quartz plate geometry was used in all experiments. Each measurement was carried out with 0.4 ml of the polymer solution containing 0.1% (weight/volume) Irgacure® 2959 initiator. UV light (365 nm) was applied by a circular multi-diode array (Moritex, Japan). The testing conditions for all measurements were 2% strain at an oscillation frequency of 1 Hz.

Water Uptake Measurements:

Hydrogel constructs were made from a volume of 100 μl polymer-fibrinogen conjugate solution with 0.1% (weight/volume) Irgacure® 2959 initiator in a 5 mm diameter silicon tube. The constructs were cross-linked under UV light (365 nm, 4-5 mW/cm$^2$) to form a 5 mm tall cylinder. FF127 was cross-linked at a temperature of 4° C., 21° C. or 37° C. The water uptake was evaluated by calculating the swelling ratio ($Q_M$), i.e., the ratio of the wet weight (mass after swelling) divided by the dry weight (weight after lyophilization).

Biodegradation Measurements:

Biodegradation of the hydrogels was characterized by fluorometrically labeling the biological component in the bio-synthetic hydrogel with amine-reactive N-hydroxysuccinimide-fluorescein (NHS-fluorescein). The rate of degradation was quantified by measuring the release of the protein during the enzymatic dissolution of the hydrogel. 100 μl hydrogel plugs were stained overnight in a PBS solution containing 0.05 mg/ml NHS-fluorescein, and washed extensively to remove unbound fluorescein. The plugs were then transferred into 3 ml of PBS with 0.01 mg/ml trypsin and 0.1% sodium azide (Riedel-deHaen, India), and incubated at 37° C. with continuous agitation. Fluorescence measurements were carried out in a Thermo Varioskan Spectrophotometer (excitation wavelength 494 nm, emission wavelength 518 nm) with Skanit2.2® Software. After the last time point, each hydrogel was hydrolytically dissociated by adding 0.1 M NaOH. After 30 minutes, the emission values were recorded at 100% degradation. Labeled hydrogel plugs without enzyme and unstained plugs with enzyme solution were used as negative controls.

Preparation of Cell-Seeded Constructs:

Cell-seeded hydrogel constructs were prepared by UV-induced cross-linking of FF127 or FT1307 conjugates in solution in the presence of dispersed human foreskin fibroblasts or HeLa cells. The passaged cells were trypsinized and suspended in 100 μl of a solution of the conjugate at a concentration of 10$^6$ cells/ml, along with a photoinitiator (0.1% w/v). The disc-shaped constructs were exposed to UV light for 5 minutes at 4° C., 21° C. or 37° C. Control cell-seeded constructs were prepared from PEG (12 kDa)-fibrinogen, F127 poloxamer diacrylate or T1307 tetraacrylate (3% w/w in PBS). The cell-seeded constructs were cultured for up to 6 days in Dulbecco's modified Eagle medium (DMEM) containing 10% fetal bovine serum (FBS), 1% penicillin-streptomycin, 1% non essential amino acids, and 0.2% 2-mercaptoethanol.

Light Microscopy and Fluorescent Microscopy:

Light microscopy and fluorescent microscopy were performed using an Eclipse TE2000-S microscope (Nikon) or an Eclipse TS100 microscope (Nikon), and a digital camera.

Statistical Analysis:

Statistical analysis was performed using Microsoft Excel statistical analysis software. Data from independent experiments were quantified and analyzed for each variable. Comparisons between two treatments were made using student's T-test (two tail, equal variance) and comparisons between multiple treatments were made with analysis of variance (ANOVA). A p-value of <0.05 was considered to be statistically significant.

Example 1

F127 Poloxamer-Fibrinogen Conjugate

Fibrinogen was conjugated to F127 poloxamer-diacrylate (prepared as described hereinabove, and as depicted in FIG. 1A) by a Michael-type addition reaction, as depicted in FIG. 1B. In order to compare the properties of poloxamer-protein conjugates with those of poly(ethylene glycol) (PEG)-protein conjugates, fibrinogen was conjugated with 12 kDa PEG-diacrylate (prepared as described hereinabove), using the same reaction.

A 3.5 mg/ml solution of fibrinogen in 150 mM phosphate buffer saline (PBS) with 8 M urea was supplemented with tris(2-carboxyethyl)phosphine hydrochloride (TCEP) at a molar ratio of 1.5:1 TCEP to fibrinogen cysteine residues. PBS with 8 M urea and 280 mg/ml of the functionalized polymer (F127-DA or PEG-DA) was then added at a molar ratio of 4:1 polymer molecules to fibrinogen cysteine residues. The mixture was allowed to react for 3 hours at room temperature. The conjugated protein was then precipitated by adding 4 volumes of acetone. The precipitate was redissolved in PBS containing 8 M urea at a protein concentration of 10 mg/ml and then dialyzed against PBS for 2 days at 4° C., with the PBS being replaced twice per day. The dialysis tubing had a cutoff of 12-14-kDa (Spectrum).

In order to establish total concentration of the F127-fibrinogen and PEG-fibrinogen conjugates, 0.5 ml of the conjugate solution was lyophilized for 24 hours and weighed. The net fibrinogen concentration was determined using a standard B CAT™ Protein Assay (Pierce Biotechnology) and the concentrations of the conjugates (dry weight) and fibrinogen were compared in order to determine the concentration of synthetic polymer in the conjugates. The efficiency of the conjugation reaction ($\epsilon_{conjugation}$) was calculated based on the concentrations and molecular weights of the synthetic polymer and fibrinogen, assuming a theoretical maximum of 29 synthetic polymer molecules per fibrinogen molecule (as fibrinogen comprises 29 thiol groups), to using the following formula:

$$\varepsilon_{conjugation} = \frac{[S.\text{Polymer}]}{[\text{Fibrinogen}]} \times \text{theortical}\left\{\frac{MW_{fibrinogen}}{29 \times MW_{S.Polymer}}\right\}$$

The mean fibrinogen concentration and conjugation efficiency obtained for 4 batches of each of F127-fibrinogen and PEG-fibrinogen conjugates are summarized in Table 1.

TABLE 1

Mean fibrinogen concentration and conjugation efficiency of synthetic polymer-fibrinogen conjugates (mean ± standard error of the mean)

| Synthetic polymer | MW (kDa) | Fibrinogen concentration (measured) (mg/ml) | Conjugate concentration (measured) (mg/ml) | Synthetic polymer concentration (calculated) (mg/ml) | Conjugation efficiency ($\epsilon_{conjugation}$) (%) |
|---|---|---|---|---|---|
| F127-DA | 12.6 | 7.7 ± 0.5 | 21 ± 2.3 | 13 ± 1.9 | 79 ± 8.4 |
| PEG-DA | 12 | 8.9 ± 2 | 24.7 ± 6.7 | 15.8 ± 4.8 | 83.8 ± 10.5 |

As shown in Table 1, both F127 poloxamer and PEG were conjugated to fibrinogen with a relatively high conjugation efficiency. There was no statistically significant difference between the conjugation efficiency or fibrinogen concentration obtained with F127 poloxamer and PEG.

Example 2

Rheological Properties of F127 Poloxamer-Fibrinogen Conjugate (FF127) and Hydrogels Formed by Cross-linking FF127

The rheological properties of the F127 poloxamer-fibrinogen conjugate (FF127) described in Example 1 was studied, as described in the Materials and Methods section hereinabove.

As shown in FIG. 2, the shear storage modulus (G') of FF127 increased considerably at temperatures above about 20° C. The transition was dependent on the concentration of FF127, as the storage modulus of 8 mg/ml FF127 increased at a slightly lower temperature than did the storage modulus of 4 mg/ml FF127.

As further shown in FIG. 2, the increase in the shear storage modulus was accompanied by a peak in the shear loss modulus (G") of the FF127.

As shown in FIG. 3A, the shear storage modulus was repeatedly increased (up to about 185 Pa) and decreased by raising the temperature to 37° C. and lowering the temperature to 15° C., indicating a reversible transition.

These results indicates that FF127 undergoes a reverse thermal gelation (RTG) phase transition at such temperatures, as a result of the formation of a continuous polymeric matrix due to physical (i.e., non-covalent) cross-linking of FF127 molecules, as depicted in FIG. 4.

It is notable that the reverse thermal gelation occurred at concentrations of less than 20 mg/ml of conjugate (corresponding to a fibrinogen concentration of approximately 8 mg/ml), as F127 does not exhibit reverse thermal gelation at concentrations less than 14.6% (w/w) [Cohn et al., *Biomacromolecules* 2005, 6:1168-1175].

Chemical (i.e., covalent) cross-linking of the FF127 molecules was performed by adding 0.1% (weight/volume) Irgacure® 2959 initiator to FF127 solutions, and irradiating the solution with UV light (365 nm, 4-5 mW/cm$^2$).

As shown in FIG. 5, chemical cross-linking of FF127 resulted in an irreversible increase in the storage modulus.

This result indicates that a hydrogel is formed due to UV-initiated free radical polymerization of the acryl functional groups on the FF127 molecules.

As shown in FIG. 6, the chemically cross-linked hydrogel exhibited temperature-dependent increases in the storage modulus and loss modulus.

As shown in FIG. 3B, the storage modulus of the chemically cross-linked hydrogel was repeatedly increased (up to about 300 Pa) and decreased by raising the temperature to 37° C. and lowering the temperature to 15° C., indicating a reversible transition.

This result indicates that the chemically cross-linked hydrogel further exhibits RTG phase transitions due to physical cross-linking of FF127 unimers, as observed in FF127 without chemical cross-linking.

As further shown in FIGS. 3A and 3B, the gelation of FF127 and chemically cross-linked FF127 at 37° C. was gradually eliminated in the presence of collagenase (which degrades fibrinogen), in a dose-dependent manner.

These results indicate that the reverse thermal gelation of both FF127 and chemically cross-linked FF127 is associated with the molecular weight of the fibrinogen which forms the backbone of the FF127. As the fibrinogen was proteolytically degraded by the collagenase, the FF127 unimers become smaller and the ability to form a physical polymeric matrix was thereby affected.

In order to explore the stability of the hydrogel network properties under applied loading conditions, hydrogels were prepared from FF127 (8 mg/ml) with or without chemical cross-linking and exposed to time-sweep rheological measurements as the applied shear stress levels were increased incrementally.

As shown in FIG. 7, the chemically cross-linked hydrogel was more responsive to temperature changes compared to the physical hydrogel, exhibiting a higher storage modulus at 37° C., but it collapsed under less oscillatory stress (70 Pa) than did the physical hydrogel (200 Pa).

As further shown therein, when the applied stress was removed at 37° C., the chemically cross-linked hydrogel was restored almost completely, whereas the physically cross-linked hydrogel recovered only slightly from the applied stress. However, lowering the temperature to 15° C. and raising it back to 37° C. completely restored the mechanical properties of both hydrogels.

These results indicate that the properties of the gels can be "reset" by lowering and raising the temperature.

Example 3

Effect of Cross-linking Temperature on Physical Properties of F127 Poloxamer-Fibrinogen Conjugate (FF127) Hydrogels As the interactions between molecules of the FF127 conjugate are temperature-dependent, it was hypothesized that the temperature during the chemical cross-linking reaction ($T_{cl}$) influences the chemical cross-linking reaction. The chemical cross-linking of a hydrogel network in the presence of free radicals may depend upon the mobility of the molecular precursors and their likelihood to form chemical cross-links when undergoing a temperature-dependent physical transition.

Hydrogels were formed by UV-activated cross-linking, as described in Example 2, at different temperatures.

As shown in FIG. 8, the G' value of the hydrogels at 37° C. was inversely proportional to the temperature at which the UV-induced cross-linking was performed. As further shown therein, the G' values of hydrogels chemically cross-linked at different temperatures were nearly identical at 15° C.

These results indicate that physical cross-linking has a highly significant effect on the physical properties which characterize chemically cross-linked networks, as the properties of the various hydrogels varied considerably at 37° C., when physical cross-linking is present, but not at 15° C., when physical cross-linking is absent.

Example 4

Water Uptake by F127 Poloxamer Fibrinogen Conjugate (FF127) Hydrogels

Water uptake of cross-linked FF127 hydrogel constructs was determined as described in the Materials and Methods section hereinabove. FF127 was cross-linked at a temperature of 21° C. or at a temperature of 37° C. As a control, water uptake of cross-linked PEG (12 kDa)-fibrinogen hydrogels was determined as described hereinabove.

The water uptake in each hydrogel represents a characteristic measure of its equilibrium state between water and polymeric matrix, and gives an indication of the structural forces involved in forming and sustaining the hydrogel network. The swelling ratio ($Q_M$) was measured for the three hydrogels at two separate ambient temperatures, 4° C. and 37° C.

As shown in FIG. 9, there was no significant difference in swelling ratio between the different hydrogels at 4° C., whereas at 37° C., FF127 and PEG-fibrinogen exhibit significantly different properties. FF127 hydrogels expelled water when warmed to 37° C., whereas PEG-fibrinogen hydrogels did not.

As shown in FIGS. 9, 10A and 10B, FF127 cross-linked at 21° C. expelled more water than did FF127 cross-linked at 37° C.

These results indicate that at a temperature at which reverse thermal gelation effects are negligible (e.g., 4° C.), the different cross-linked polymers exhibit similar properties, whereas at a temperature at which reverse thermal gelation effects are significant (e.g., 37° C.), the degree of reverse thermal gelation affects the swelling properties of the polymer networks.

Example 5

Comparison of Biodegradation and Rheological Properties of F127 Poloxamer-Fibrinogen Conjugate (FF127) Hydrogels The biodegradation kinetics of chemically cross-linked FF127 and PEG (12 kDa)-fibrinogen hydrogels were determined in a 0.01 mg/ml trypsin solution at 37° C., as described hereinabove. FF127 hydrogels were cross-linked at temperatures of 21° C. and 37° C. were compared. The hydrogels were cross-linked by exposure to UV, as described hereinabove.

The storage moduli of the hydrogels were determined as described hereinabove. For comparison, a hydrogel was prepared by cross-linking F127 diacrylate at 37° C. the storage modulus was determined As shown in FIG. 11, there was a statistically significant difference between the three materials in terms of their biodegradation rate ($p<0.05$). The hydrogels made of PEG-fibrinogen degraded the fastest, with a half-life of 105±5.4 minutes, and were fully degraded after 24 hours in 0.01 mg/ml trypsin. The hydrogels made of FF127 reached only ~60% degradation after 24 hours. The half-life of the FF127 hydrogels was 420±66 minutes when cross-linked at 37° C., and 580±90 minutes when cross-linked at 21° C.

As shown in FIG. 12, the storage modulus of FF127 cross-linked at 37° C. was similar to that of the PEG-fibrinogen, and considerably lower than that of the FF127 cross-linked at 21° C. As further shown therein, the storage modulus of FF127 cross-linked at 21° C. was similar to that of F127 diacrylate cross-linked at 37° C.

Thus, although the biodegradation rate of cross-linked FF127 was lower than that of cross-linked PEG-fibrinogen, and was only moderately affected by the cross-linking temperature, the storage modulus of cross-linked FF127 was strongly affected by the cross-linking temperature.

These results indicate that factors determining biodegradation rate (e.g., type of polymer) can be selected relatively independently of the factors determining rheological properties (e.g., cross-linking temperature).

Example 6

Tetronic® T1307-Fibrinogen Conjugate

Fibrinogen was conjugated to Tetronic® T1307 tetraacrylate (prepared as described hereinabove) by a Michael-type addition reaction, using essentially the same procedures as described in Example 1. As depicted in FIGS. 13A and 13B, conjugation of a tetraacrylate polymer to fibrinogen results in 3 free acrylate groups per conjugated polymer (1 acrylate group attaches the fibrinogen to the polymer), providing increased cross-linking ability.

The mean fibrinogen concentration and conjugation efficiency was determined for 4 batches of T1307-fibrinogen, as described in Example 1.

The obtained solution of T1307-fibrinogen conjugate comprised 20.4±1.4 mg/ml of the conjugate, 6.7±1 mg/ml fibrinogen, and 13.7±0.5 mg/ml synthetic polymer. The conjugation efficiency was 66.3±8.5%.

Example 7

Physical Properties of T1307-Fibrinogen (FT1307) Hydrogels

The T1307-fibrinogen conjugate (FT1307) described in Example 6 was chemically cross-linked by UV light at a concentration of 6 mg/ml, at temperatures of 4° C., 21° C. or 37° C. Rheological properties, water uptake and biodegradation of the obtained hydrogels were determined, as described hereinabove.

As shown in FIGS. 14A and 14B, the cross-linking temperature of FT1307 was inversely correlated to the storage modulus at 37° C.

As shown in FIG. 15, the cross-linking temperature of FT1307 was inversely correlated to the amount of water expelled from the hydrogel when the hydrogel was warmed to 37° C. In contrast, the cross-linking temperature had little effect on the water uptake of the polymers at 4° C.

In contrast, as shown in FIG. 16, the cross-linking temperature of FT1307 did not exhibit any clear correlation with the degradation rates of the FT1307.

These results are similar to those presented in Examples 3 and 4, and indicate that the cross-linking temperature can be used to determine the properties of polymer-protein hydrogels formed using a variety of reverse thermal gelation polymers, and that the rheological properties of the hydrogels can be determined independently of the degradation rates.

Example 8

Cell-seeded F127-Fibrinogen (FF127) Hydrogels

Cell-seeded hydrogel constructs were prepared by UV-induced cross-linking of a FF127 conjugate solution in the presence of dispersed human foreskin fibroblasts (Lonza, Walkersville, Md., USA), as described in the Materials and Methods section. Control cell-seeded constructs were prepared from PEG (12 kDa)-fibrinogen and F127 poloxamer diacrylate. Samples for histology were fixed in 4% formalin on day 3 and on day 6 of each experiment. Cross-sections were stained with hematoxylin and eosin (H & E) for imaging.

As shown in FIG. 17, the formation of lamellipodia and a spindled cellular morphology proceeded more rapidly in FF127 cross-linked at 37° C. than in FF127 cross-linked at 21° C. On day 3, the cells in FF127 cross-linked at 21° C. were relatively rounded and had only begun to form lamellipodia, whereas in the FF127 cross-linked at 37° C., the cells were highly spindled with many cellular lamellipodia. Accordingly, on day 6, the cells in FF127 cross-linked at 21° C. had begun to invade the matrix through cellular lamellipodia, but only a few were fully spindled, whereas most of the cells in FF127 cross-linked at 37° C. were fully spindled and exhibited many lamellipodia.

As further shown therein, in the cross-linked PEG-fibrinogen, which is characterized both by a relatively high biodegradability and low storage modulus (as shown hereinabove), cells were highly spindled by day 3.

As further shown therein, in cross-linked F127 diacrylate, which lacks fibrinogen, cells remained completely rounded and did not form cellular extensions.

Cell-seeded FF127 hydrogel constructs were also prepared by physical cross-linking at 37° C. without chemical cross-linking by UV light. The cells in such hydrogels were compared to those in FF127 hydrogel constructs chemically cross-linked at 37° C.

As shown in FIG. 18, cells in FF127 hydrogels with only physical cross-linking and cells in FF127 hydrogels with both physical and chemical cross-linking both displayed a similar morphology. On day 3 in both materials, the cells exhibited spindled morphology with protrusions invading the matrix, and on day 6 in both materials, the cells were fully spread and highly spindled.

The viability of the encapsulated cells was determined on day 0 and on day 3 of each experiment. The cells were removed from the construct by dissolving the fibrinogen in 0.4 mg/ml collagenase 1A solution for 4 hours followed by 5 minutes centrifugation (1000 rotations per minute). The pellet was redissolved in 100 μl of staining solution containing 0.004 mM ethidium homodimer-1 and 2 mg/ml Hoechst 33342 in PBS. The cells were stained for 30 minutes on an orbital shaker in the dark and then centrifuged for 5 minutes (1000 rotations per minute). The cell pellet was dissolved in 25 μl of PBS, and imaged on a glass microscope slide overlaid with a cover slip. The stained cells were imaged by fluorescent microscopy. The live and dead cells were counted and normalized by a control suspension that was not exposed to UV light.

As shown in FIG. 19, the viability of cells in chemically cross-linked FF127 was at least 88% on day 0 and at least 85% on day 3. The cell viability on both days was higher in FF127 cross-linked at 37° C. than in FF127 cross-linked at 21° C., although the differences were not statistically significant.

The above results indicate that hydrogels formed from poloxamer-fibrinogen conjugates, including hydrogels with and without chemical cross-linking of the conjugates, can serve as matrices for cell growth and invasion. The results further indicate that the rate of cell invasion can be modulated by selecting the physical properties of the gel, for example, by selecting a suitable cross-linking temperature.

Example 9

Cellular Outgrowth into F127-Fibrinogen (FF127) Hydrogels

Outgrowth experiments were performed using a dense tissue construct made from compacted bovine aortic smooth muscle cells (Genlantis) seeded in collagen gels. Each compacted cell-seeded collagen gel was encapsulated inside an FF127 hydrogel. As a control, a compacted cell-seeded collagen gel was encapsulated inside a PEG-fibrinogen hydrogel.

The collagen-based tissue was made from a solution of 5×DMEM, 10% fetal bovine serum, reconstituted collagen type-I solution in 0.02 N acetic acid (2 mg/ml), and 1 M NaOH with smooth muscle cells dispersed at a concentration of $3\times10^6$ cells/ml. The cell-seeded collagen gels were cultured for 2 days in culture medium before the compacted tissue was placed in 300 μl of FF127 (or PEG-fibrinogen) conjugate solution and photoinitiator in a 48-well plate. After exposure to 5 minutes of UV light at 37° C. or 21° C., the encapsulated tissue was cultured inside the hydrogel with 500 μl of culture medium. The cellular outgrowth from the collagen gel into the FF127 (or PEG-fibrinogen) encapsulating matrix was monitored daily for up to 5 days. The outgrowth results were quantified by measuring the average travel distance of the cells from the margins of the dense collagen tissue into the FF127 (or PEG-fibrinogen) hydrogel using phase contrast micrographs of the samples taken at set time intervals.

As shown in FIGS. 20A and 20B, in each of the three tested materials (FF127 cross-linked at 21° C. and at 37° C., and cross-linked PEG-fibrinogen), the cells began to invade the matrix surrounding the tissue mass after 1 day and continued to invade the matrix for the duration of the experiment.

As shown in FIG. 20B, the rate of invasion in the FF127 cross-linked at 37° C. remained constant for the duration of the experiment, whereas the rate of invasion decreased in the FF127 cross-linked at 21° C. and in the PEG-fibrinogen, starting on the third day of the experiment. Beginning from day 3, there was a statistically significant difference between the cell migration distance in FF127 cross-linked at 21° C. and in FF127 cross-linked at 37° C. On day 4, the distance the cells traveled was 21% lower in FF127 cross-linked at 21° C. than in FF127 cross-linked at 37° C., and on day 5, the distance was 11% lower in FF127 cross-linked at 21° C. The invading cells did not exhibit a morphological difference among the three materials tested.

These results further indicate that the rate of cell invasion can be modulated by selecting the physical properties of the gel.

Example 10

Cell-seeded T1307-Fibrinofen (FT1307) Hydrogels

Cell-seeded hydrogel constructs were prepared by UV-induced cross-linking of a FT1307 conjugate solution in the presence of human foreskin fibroblasts and HeLa human adenocarcinoma cells, as described in the Materials and Methods section. Control cell-seeded constructs were prepared from T1307 tetraacrylate.

In order to view the seeded cells and determine their viability, the cell-seeded constructs were placed in a well holding 2 ml of 4 mM calcein AM and 2 mM ethidium homodimer-1 in DMSO, and incubated for 45 minutes. Viable cells are stained by calcein and non-viable cells are stained by ethidium. Each construct was then washed twice for 15 minutes in PBS in order to remove excess dye molecules. The cells were then imaged by fluorescent microscopy.

As shown in FIG. 21, cell spreading of fibroblasts proceeded relatively rapidly in FT1307 cross-linked at 37° C., and more slowly in FT1307 cross-linked at 21° C., and was almost completely halted in FT1307 cross-linked at 4° C. The rate of cell spreading was inversely correlated to the storage modulus, which was 52 Pa, 244 Pa and 373 Pa following cross-linking temperatures of 37° C., 21° C. and 4° C., respectively.

As further shown in FIG. 21, cell viability was high in all three types of FT1307 matrices, as evidenced by the paucity of ethidium (orange-colored) staining.

As shown in FIG. 22, HeLa cell colonies were relatively dense and confined in FT1307 cross-linked at 4° C., somewhat less dense and confined in FT1307 cross-linked at 21° C., and relatively disperse in FT1307 cross-linked at 37° C.

The above results indicate that the rate of cell spreading and the structure of cell colonies is affected by the physical properties of the matrix, which can be determined by cross-linking temperature.

Example 11

Cellular Outgrowth in F127-Fibrinogen (FF127) Hydrogels Encapsulated within T1307-Fibrinofen (FT1307) Hydrogels Outgrowth experiments were performed using FF127 physically cross-linked capsules containing cultures or co-cultures of human dermal fibroblasts and HeLa cells, which were entrapped in FT1307 chemically cross-linked hydrogels. Trypsinized cells were suspended in 500 μl of FF127 conjugate solution at a concentration of $10^7$ cells/ml, and loaded into a Micro-Fine™ 30 G syringe (BD, New Jersey, USA).

As shown in FIG. 23A, while keeping the temperature below 20° C., drops 20 of the suspension of cells in FF127 were added from syringe 10 into a gently stirred phosphate buffered saline (PBS) medium 30 kept at a temperature of 37° C. The drops 20 gelled upon exposure to a temperature of 37° C. in PBS medium 30, forming cell-seeded capsules 40. The cell-seeded capsules 40 were isolated and incubated in DMEM cell culture medium for 2 days at 37° C., and then seeded in 300 μl of FT1307 conjugate solution with a photoinitiator (0.1% w/v), and exposed to UV light for 5 minutes at temperatures of 37° C., 21° C. or 4° C.

As shown in FIG. 23B, this procedure resulted in a co-polymeric construct—so as to entrap the relatively soft physically cross-linked FF127 capsules 50 within a harder chemically cross-linked FT1307 milieu 60.

As described hereinabove, cross-linking temperatures of 37° C., 21° C. or 4° C. resulted in FT1307 storage moduli of 52 Pa, 244 Pa and 373 Pa, respectively.

As shown in FIGS. 24A and 24B, fibroblasts exhibited outgrowths in a hydrogel with a low storage modulus (52 Pa), but not in a hydrogel with a high storage modulus (373 Pa).

In comparison, as shown in FIGS. 25A and 25B, HeLa cells exhibited different migration/invasion strategies in hydrogels with different moduli; the cells exhibited individual amoeboid migration in a hydrogel with a low storage modulus (52 Pa), and collective multicellular migration in a hydrogel with a high storage modulus (373 Pa).

Co-cultures of HeLa cells and fibroblasts were seeded in FF127 capsules within FT1307 hydrogels in order to assess how the hydrogel modulus affects the development of heterogenic cultures. In order to differentiate between the fibroblasts and HeLa cells, GFP (green fluorescent protein)-labeled fibroblasts and DiI (1,1'-dioctadecyl-3,3,3'3'-tetramethylindocarbocyanine perchlorate)-stained HeLa cells were co-cultured.

As shown in FIGS. 26A and 26B, in an FT1307 hydrogel with a high storage modulus (373 Pa), HeLa cells pushed into the FT1307 hydrogel, increasing the diameter of the capsule, whereas fibroblast outgrowth was halted.

As shown in FIGS. 27A and 27B, in an FT1307 hydrogel with a low storage modulus (52 Pa), the capsule front was dominated by fibroblasts, which effectively performed mesenchymal migration into the FT1307 hydrogel.

The above results indicate that the outgrowth of cells from homogeneous and heterogeneous cultures can be modulated according to the physical properties of a surrounding hydrogel.

The above results further indicate that heterogeneous hydrogels can be prepared from more than one type of polymer-protein conjugate.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A conjugate comprising a polypeptide having attached thereto at least two polymeric moieties, each of said polymeric moieties exhibiting a reverse thermal gelation, wherein said polypeptide comprises an extracellular matrix protein or a fragment thereof.

2. The conjugate of any of claim 1, wherein at least one of said polymeric moieties further comprises at least one cross-linking moiety for covalently cross-linking a plurality of molecules of the conjugate to one another.

3. The conjugate of any of claim 1, being of the general formula:

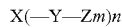

wherein:
X is said polypeptide;
Y is said polymeric moiety;
Z is a cross-linking moiety;
n is an integer greater than 1; and
m is 0, 1 or an integer greater than 1.

4. The conjugate of claim 1, wherein said polypeptide comprises a fibrinogen or a fragment thereof.

5. The conjugate of claim 1, wherein said protein is denatured.

6. The conjugate of any of claim 1, wherein of said polymeric moieties comprises a synthetic polymer.

7. The conjugate of claim 6, wherein each of said polymeric moieties comprises a poloxamer (poly(ethylene oxide-propylene oxide) copolymer).

8. The conjugate of claim 7, wherein said poloxamer is F127 poloxamer.

9. The conjugate of claim 1, wherein said cross-linking moiety comprises a polymerizable group.

10. The conjugate of claim 1, wherein said polypeptide is denatured fibrinogen and said polymeric moieties comprise F127 poloxamer.

11. The conjugate of claim 1, identified for use in generating a scaffold.

12. A composition-of-matter comprising a cross-linked form of the conjugate of claim 1, said cross-linked form comprising a plurality of molecules of the conjugate cross-linked to one another.

13. The composition-of-matter of claim 12, being a hydrogel.

14. The composition-of-matter of claim 12, generated by a reverse thermal gelation of said plurality of molecules of the conjugate in an aqueous solution.

15. The composition-of-matter of claim 12, wherein said plurality of molecules of the conjugate are non-covalently cross-linked to one another.

16. The composition-of-matter of claim 12, wherein at least one of said polymeric moieties further comprises a cross-linking moiety, and said plurality of molecules of the conjugate are covalently cross-linked to one another.

17. The composition-of-matter of claim 16, being capable of undergoing a reverse thermal gelation.

18. The composition-of-matter of claim 12, further comprising cells therein.

19. A process of producing the composition-of-matter of claim 12, the process comprising heating a solution of a plurality of molecules of a conjugate comprising a polypeptide having attached thereto at least two polymeric moieties, said polypeptide comprising an extracellular matrix protein or a fragment thereof and each of said polymeric moieties exhibiting a reverse thermal gelation, from a first temperature to a second temperature, said second temperature being such that a reverse thermal gelation of the conjugate in said solution is effected, thereby producing the composition-of-matter.

20. The process of claim 19, wherein said composition-of-matter is produced in vivo.

21. The process of claim 19, wherein said conjugate comprises at least one polymeric moiety that further comprises at least one cross-linking moiety, the process further comprising subjecting said solution to conditions that effect cross-linking of said cross-linking moieties.

22. A process of producing the composition-of-matter of claim 16, the process comprising subjecting a solution comprising a plurality of molecules of a conjugate comprising a polypeptide having attached thereto at least two polymeric moieties, said polypeptide comprising an extracellular matrix protein or a fragment thereof and each of said polymeric moieties exhibiting a reverse thermal gelation, at least one of said polymeric moieties further comprising at least one cross-linking moiety for covalently cross-linking a plurality of molecules of the conjugate to one another, to conditions that effect covalent cross-linking of said cross-linking moieties, thereby producing the composition-of-matter.

23. The process of claim 21, wherein said covalent cross-linking is effected in vivo.

24. The process of claim 21, wherein said covalent cross-linking is effected ex vivo, to thereby produce a covalently cross-linked scaffold, the process further comprising subjecting the covalently cross-linked scaffold to a physiological temperature in vivo, such that a reverse thermal gelation of said scaffold is effected in vivo, thereby producing the composition-of-matter.

25. A process of producing the composition-of-matter of claim 16 in vivo, the process comprising:
(a) subjecting a solution comprising a plurality of molecules of a conjugate comprising a polypeptide having attached thereto at least two polymeric moieties, said polypeptide comprising an extracellular matrix protein or a fragment thereof and each of said polymeric moieties exhibiting a reverse thermal gelation, at least one of said polymeric moieties further comprising at least one cross-linking moiety for covalently cross-linking a plurality of molecules of the conjugate to one another, to conditions that effect covalent cross-linking ex vivo, to thereby produce a covalently cross-linked scaffold; and (b) subjecting said covalently cross-linked scaffold to a physiological temperature in vivo, such that a reverse thermal gelation of said scaffold is effected in vivo, thereby producing the composition-of-matter.

26. A method of controlling a physical property of a composition-of-matter of claim 12, the method comprising controlling a parameter selected from the group consisting of a concentration of a conjugate comprising a polypeptide having attached thereto at least two polymeric moieties wherein each of said polymeric moieties exhibits a reverse thermal gelation and said polypeptide comprises an extracellular matrix protein or a fragment thereof, an ambient temperature, a presence or absence of an initiator, a dose of irradiation during covalent cross-linking, and a cross-linking temperature.

27. A process of producing the conjugate of claim 1, the process comprising covalently attaching a polymer to a polypeptide, said polypeptide comprising an extracellular matrix fragment protein or a fragment thereof, said polymer and said polypeptide being such that at least two polymer molecules covalently attach to a molecule of said polypeptide, wherein each of said polymer molecules exhibits a reverse thermal gelation, thereby producing the conjugate.

28. A method of inducing formation of a tissue in vivo, the method comprising implanting the composition-of-matter of claim 12 in a subject, to thereby induce the formation of the tissue.

29. A method of inducing formation of a tissue in vivo, the method comprising implanting a plurality of molecules of the conjugate of claim 1 in a subject, to thereby induce the formation of the tissue.

30. A method of inducing formation of a tissue ex vivo, the method comprising subjecting the composition-of-matter of claim 18 to conditions conductive to growth of said cells, to thereby induce tissue formation.

31. A method of treating a subject having a disorder characterized by tissue damage or loss, the method comprising implanting the composition-of-matter of claim 12 in a subject, to thereby induce formation of said tissue, thereby treating the disorder characterized by tissue damage or loss.

32. A method of treating a subject having a disorder characterized by tissue damage or loss, the method comprising implanting a plurality of molecules of the conjugate of claim 1 in a subject, to thereby induce formation of said tissue, thereby treating the disorder characterized by tissue damage or loss.

33. A pharmaceutical, cosmetic or cosmeceutical composition comprising a plurality of molecules of the conjugate of claim 1, the composition being identified for use in inducing formation of a tissue upon being contacted with a tissue and further upon subjecting said composition to a physiological temperature.

34. The pharmaceutical, cosmetic or cosmeceutical composition of claim 33, wherein said conjugate comprises at least one cross-linking moiety, the composition being identified for use in inducing formation of a tissue upon further subjecting said plurality of molecules of said conjugate to conditions that effect covalent cross-linking of said cross-linking moiety.

35. The pharmaceutical, cosmetic or cosmeceutical composition of claim 34, further comprising an initiator for inducing said covalent cross-linking of said cross-linking moiety.

36. The pharmaceutical, cosmetic or cosmeceutical composition of claim 33, packaged in a packaging material and identified in print, in or on said packaging material, for use in inducing formation of said tissue.

37. A kit for inducing formation of a tissue, the kit comprising:

(a) the conjugate of claim 1;

(b) an aqueous solvent; and (c) instructions for cross-linking an aqueous solution of said conjugate in order to form a scaffold for inducing formation of said tissue.

38. The kit of claim 37, wherein said conjugate comprises at least one cross-linking moiety, the kit further comprising an initiator for inducing covalent cross-linking of said cross-linking moiety.

* * * * *